United States Patent
Iwanaga et al.

(10) Patent No.: US 8,815,595 B2
(45) Date of Patent: Aug. 26, 2014

(54) SUBSTRATE FOR FORMING A THREE-DIMENSIONAL TISSUE CONSTRUCT AND METHOD OF USE

(75) Inventors: Hiroshi Iwanaga, Kanagawa (JP); Kentaro Shiratsuchi, Tokyo (JP); Koji Nakazawa, Fukuoka (JP); Masatsugu Shimomura, Hokkaido (JP)

(73) Assignee: FUJIFILM Corporation, Tokyo (JP)

( * ) Notice: Subject to any disclaimer, the term of this patent is extended or adjusted under 35 U.S.C. 154(b) by 1338 days.

(21) Appl. No.: 12/033,324

(22) Filed: Feb. 19, 2008

(65) Prior Publication Data

US 2008/0215073 A1 Sep. 4, 2008

(30) Foreign Application Priority Data

Feb. 20, 2007 (JP) ................. 2007-039992

(51) Int. Cl.
*C12M 3/00* (2006.01)
(52) U.S. Cl.
USPC .......................................... 435/402; 435/401
(58) Field of Classification Search
CPC .............................. C12N 5/0068; C12N 5/067
USPC ....................................... 435/401, 402, 297.1
See application file for complete search history.

(56) References Cited

U.S. PATENT DOCUMENTS

| 5,385,836 A | 1/1995 | Kimura et al. | |
|---|---|---|---|
| 2003/0215941 A1* | 11/2003 | Campbell et al. | ............. 435/325 |
| 2004/0197907 A1 | 10/2004 | Kataoka et al. | |
| 2007/0122901 A1* | 5/2007 | Morita et al. | ................. 435/325 |

FOREIGN PATENT DOCUMENTS

| EP | 0 402 272 A2 | 12/1990 | |
|---|---|---|---|
| EP | 0 513 803 A2 | 11/1992 | |
| EP | 0 529 751 A1 | 3/1993 | |
| EP | 1 428 871 A1 | 6/2004 | |
| EP | 1 686 171 A1 | 8/2006 | |
| EP | 1693075 | * 8/2006 | ............. A61L 27/56 |
| JP | 02-013370 A | 1/1990 | |
| JP | 03010674 A | 1/1991 | |
| JP | 3010674 B2 | 2/2000 | |
| JP | 2001-157574 A | 6/2001 | |
| JP | 3270286 B2 | 1/2002 | |
| JP | 2002-335949 A | 11/2002 | |
| WO | 03/010302 A1 | 2/2003 | |
| WO | WO 2005/038011 | * 4/2005 | ............... C15N 5/00 |

OTHER PUBLICATIONS

Jitsutaro Kawaguchi, "Generation of Osteoblasts and Chondrocytes From Embryonic Stem Cell", Methods in Molecular Biology, 2006, pp. 135 and 139-141, vol. 330, Embryonic Stem Cell Protocols, Second, Edition vol. 2.

(Continued)

*Primary Examiner* — Allison Ford
(74) *Attorney, Agent, or Firm* — Sughrue Mion, PLLC

(57) ABSTRACT

The present invention provides a tissue construct-forming substrate for forming a three-dimensional tissue construct containing proliferating cells, the substrate including a porous film having through-holes, and the porous film having, on the surface of the film, a cell adhesive region capable of retaining cells and a cell non-adhesive region located at a peripheral region of the cell adhesive region, a tissue construct-forming kit comprising the above-mentioned tissue construct-forming substrate and a frame, and a method for forming the above-mentioned tissue construct.

14 Claims, 14 Drawing Sheets

(56) References Cited

OTHER PUBLICATIONS

Notice of Reasons for Rejection, dated Mar. 6, 2012, issued in corresponding JP Application No. 2007-039992, 5 pages in English and Japanese.

Tanaka et al., "Function Control of a Digestive System Cell using a Novel Polymer Porous Thin Film," G. I. Research, vol. 13, No. 4, 2005, pp. 263-270, 9 pages including a one-page, English-language summary.

"The Effects of a Honeycomb Film as a Cell Scaffold," The Japanese Society for Regenerative Medicine Magazine, Feb. 1, 2006, vol. 5, No. 1, pp. 96-101 and 13, 8 pages with a one-page, English-language summary.

Notice of Reasons for Rejection, dated Feb. 5, 2013, issued in corresponding JP Application No. 2007-039992, 5 pages in English and Japanese.

Communication pursuant to Article 94(3) EPC, dated Jan. 6, 2014, issued in corresponding EP Application No. 08 003 023.2, 5 pages in English.

Decision of Refusal, dated Jan. 7, 2014, issued in corresponding JP Application No. 2007-039992, 4 pages in English and Japanese.

\* cited by examiner

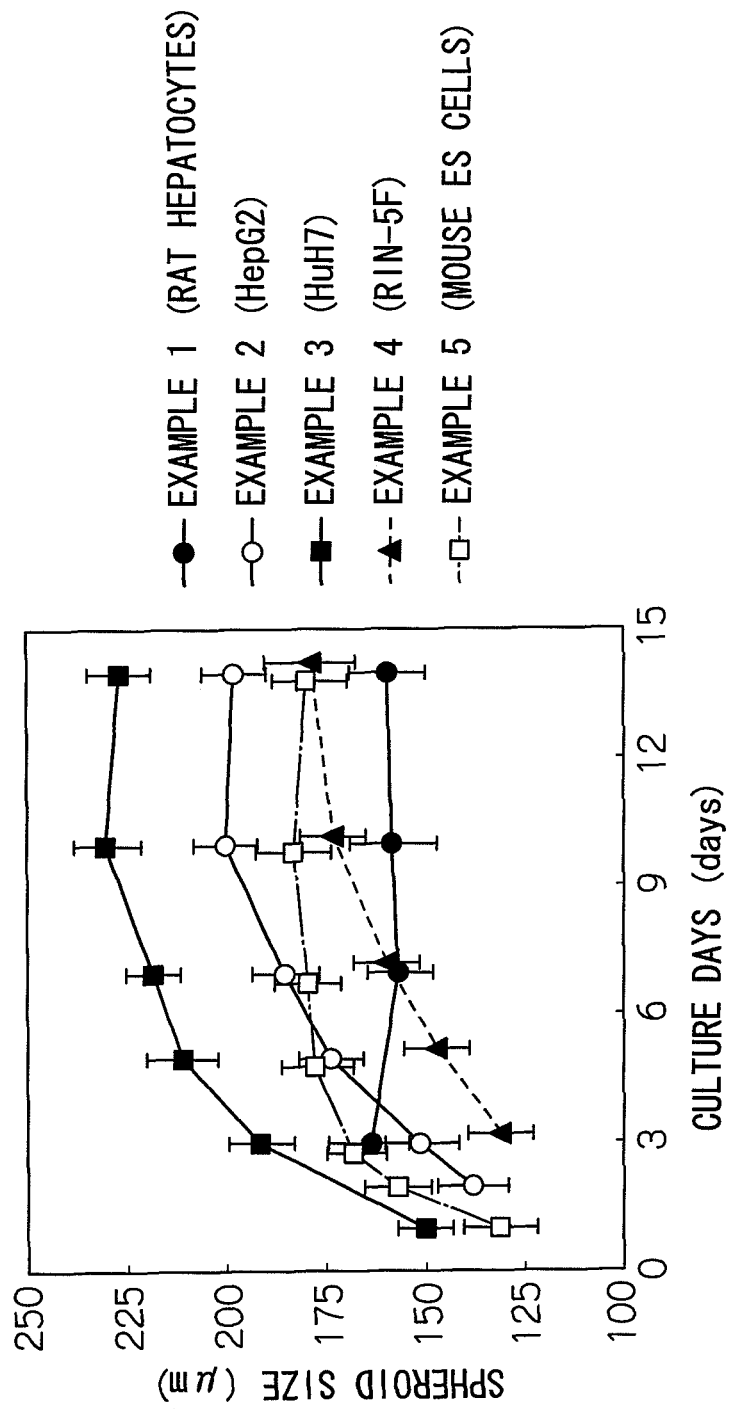

SUBSTRATE FOR FORMING A THREE-DIMENSIONAL TISSUE CONSTRUCT AND METHOD OF USE

CROSS-REFERENCE TO RELATED APPLICATION

This application claims priority under 35 USC 119 from Japanese Patent Applications No. 2007-039992, the disclosure of which is incorporated by reference herein.

BACKGROUND OF THE INVENTION

1. Field of the Invention

The present invention relates to a tissue construct-forming substrate, which is useful for forming a three-dimensional tissue construct containing proliferating cells, a tissue construct-forming kit including the substrate, a method for forming a tissue construct using the kit, and a three-dimensional tissue construct obtained by the method.

2. Description of the Related Art

It has been reported that when case where cultured cells are three-dimensionally assembled to form a tissue construct, the cells survive for a longer period of time and exhibit their original in vivo function at a higher level compared with, for example, a case where cultured cells are two-dimensionally attached to a substrate surface to form a so-called monolayer. Therefore, it is expected that a technique for forming a three-dimensional tissue construct from cultured cells is applied to, for example, a simulator for reproducing biological behavior, an alternative technique for animal experiments in drug development, a regenerative medicine technique by cell transplantation and the like.

As such a technique for forming a three-dimensional tissue construct of cultured cells, a technique in which, for example, primary hepatocytes are cultured in a well which is formed on a substrate and has a cell non-adhesive surface, whereby a tissue construct comprising the primary hepatocytes three-dimensionally assembled in the well has been heretofore proposed (see, for example, Japanese Patent No. 3270286). This document describes that by changing the number of cells inoculated into the well, the size of the tissue construct can be controlled. However, in this technique, in the case where the formed three-dimensional tissue construct contained proliferating cells, the size of the three-dimensional tissue construct continued to increase with the lapse of culture time because the cells proliferated, therefore, it was difficult to control the size of the three-dimensional tissue construct to be constant.

As another method, a technique in which after endothelial cells are two-dimensionally cultured in a plurality of small areas regularly arranged on a surface of a substrate, primary hepatocytes are cultured on a monolayer of the endothelial cells, whereby a tissue construct comprising the primary hepatocytes three-dimensionally assembled on the monolayer is formed has been proposed (see, for example, WO 03/010302). This document describes that in order to prevent a plurality of constructs formed adjacent to one another from adhering to one another, the distance between the plurality of small areas should be set to a predetermined value or more. However, a method for preventing an increase in the size of the three-dimensional tissue construct containing proliferating cells is not considered.

Further, use of a honeycomb porous body formed of a non-water-soluble polymer as a material which can be a favorable scaffold for cell proliferation has been proposed (see, for example, JP-A No. 2001-157574). However, this porous material has a honeycomb structure with a bottom, i.e., a structure in which a plurality of small spaces divided with partitions vertically disposed on a base film are formed on a surface of the base film such that they are positioned in a hexagonal manner, and it is not reported whether or not proliferated cells can maintain their function over a long period of time, or whether or not this honeycomb porous body can be used as a substrate for a cell chip capable of maintaining the function of cells over a long period of time.

On the other hand, in the case where proliferating cells with a high metabolic activity are cultured over a long period of time as a case, for example, where an embryoid body is formed from ES cells, development of a method for forming a tissue construct capable of smoothly performing supply of a fresh culture medium and discharge of waste product or a tissue construct-forming kit capable of realizing the method has been demanded. In general, for example, when a large number of embryoid bodies with a uniform size are formed from ES cells, the hanging drop method is employed (see, for example, Methods in Molecular Biology, vol. 330: Embryonic Stem Cell Protocols: Second Edition vol. 2, (2006) pp. 139-141 (Humana Press)). However, it took time and labor to form a tissue construct by employing this method, and development of an efficient method for forming a three-dimensional tissue construct or a tissue construct-forming kit capable of realizing the method has been also demanded from this viewpoint.

SUMMARY OF THE INVENTION

The present invention has been made in view of the above circumstance and provides a tissue construct-forming substrate, a tissue construct-forming kit including the substrate, a method for forming a tissue construct using the kit, and a three-dimensional tissue construct obtained by the method.

A first aspect of the present invention provides a tissue construct-forming substrate for forming a three-dimensional tissue construct containing proliferating cells, the substrate including a porous film having through-holes, and the porous film having, on the surface of the film, a cell adhesive region capable of retaining cells and a cell non-adhesive region located at a peripheral region of the cell adhesive region.

A second aspect of the present invention provides a tissue construct-forming kit for forming a three-dimensional tissue construct containing proliferating cells, the kit including the above-mentioned tissue construct-forming substrate and a frame which supports the tissue construct-forming substrate.

A third aspect of the present invention provides a method for forming a tissue construct, comprising preparing the above-mentioned tissue construct-forming substrate; and culturing proliferating cells inoculated on a surface of the tissue construct-forming substrate so as to proliferate and form a three-dimensional tissue construct.

A fourth aspect of the present invention provides a three-dimensional tissue construct obtained by culturing proliferating cells by the above-mentioned method for forming a tissue construct.

BRIEF DESCRIPTION OF THE DRAWINGS

FIG. 9 is a graph showing the change over time in the particle size of the spheroid formed in Examples 1 to 5.

DETAILED DESCRIPTION OF THE INVENTION

A tissue construct-forming substrate of the present invention is a tissue construct-forming substrate for forming a three-dimensional tissue construct containing proliferating cells, the substrate including a porous film having through-holes and the porous film having, on the surface of the film, a cell adhesive region capable of retaining cells and a cell non-adhesive region located at a peripheral region of the cell adhesive region.

Further, a tissue construct-forming kit of the invention is a tissue construct-forming kit for forming a three-dimensional tissue construct containing proliferating cells, the kit including the above-mentioned tissue construct-forming substrate and a frame which supports the tissue construct-forming substrate.

According the present invention, when proliferating cells are cultured, an increase in the size of a three-dimensional tissue construct that is formed can be prevented, even when proliferating cells are cultured, by application of a porous film having through-holes capable of smoothly supplying a fresh culture medium and discharging waste products and, further, the function of the cells can be maintained over a long period of time even if proliferating cells with a high metabolic activity are used. Therefore, a tissue construct-forming substrate useful for efficiently forming a three-dimensional tissue construct and a tissue construct-forming kit including the substrate can be provided.

Further, by using the tissue construct-forming substrate and the kit comprising the substrate of the invention, even when proliferating cells are cultured, a method for forming a tissue construct capable of efficiently forming a three-dimensional tissue construct with a controlled size and maintaining a higher activity for a longer period of time compared with related methods, and a three-dimensional tissue construct of cells obtained by the method, can be provided.

Hereinafter, the tissue construct-forming substrate and tissue construct-forming kit according to an embodiment of the invention, as well as a method for forming a tissue construct using the kit, are described with reference to drawings.

The method for forming a tissue construct according to this embodiment (hereinafter referred to as "the present method") comprises preparing at least one tissue construct-forming substrate (hereinafter occasionally referred to as "the present substrate") of the invention using a specific porous film (hereinafter referred to as a "preparation step"); and culturing proliferating and non-proliferating cells inoculated on cell adhesive regions located on a surface of the tissue construct-forming substrate to form a three-dimensional tissue construct (hereinafter referred to as a "tissue construct") containing the cells on respective surface regions (hereinafter referred to as a "culture step").

First, the preparation step of the present method is described along with the detailed structure of the present substrate.

Figure 1:
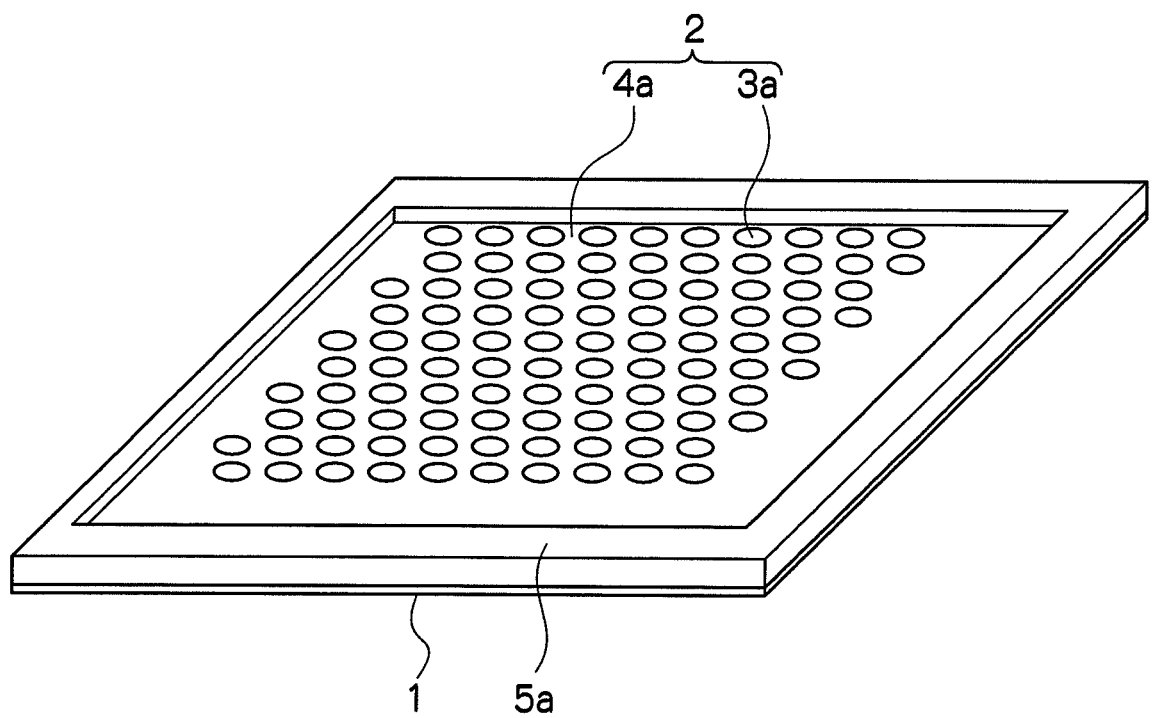
FIG. 1 is a perspective view showing an embodiment of a tissue construct-forming kit of the present invention comprising a porous film and a frame-shaped supporting member, in which the periphery of the porous film is supported by the frame-shaped supporting member.
Figure 2:
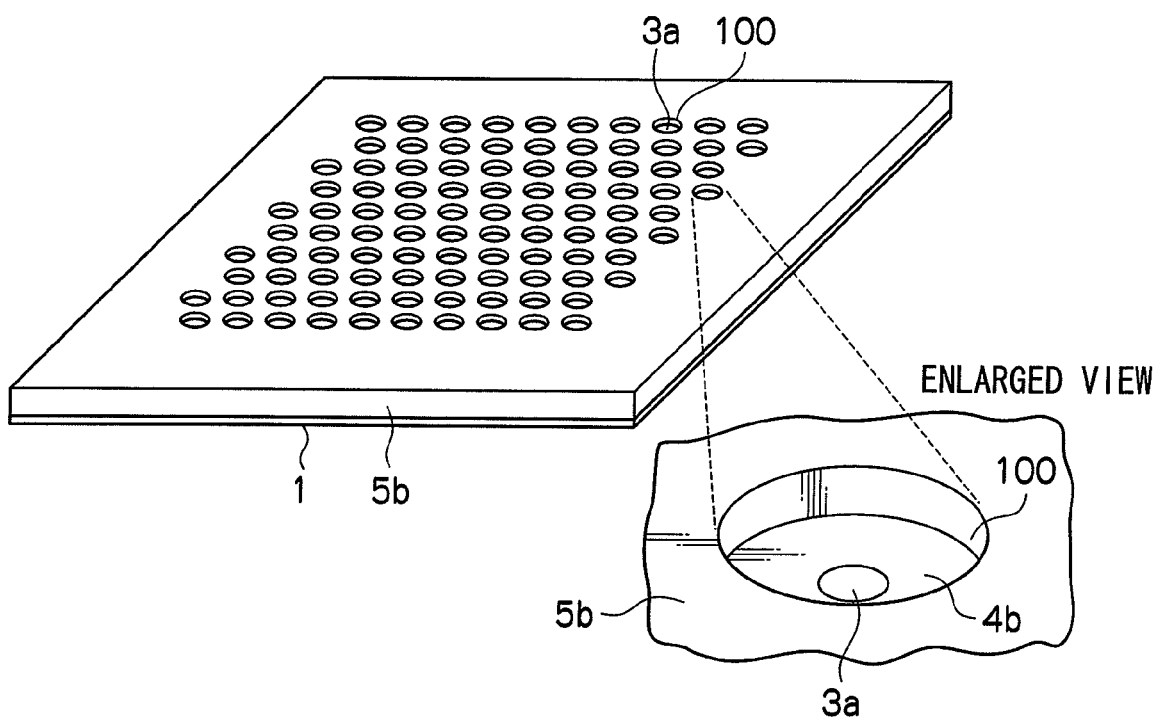
FIG. 2 is a perspective view showing another embodiment of a tissue construct-forming kit of the invention comprising a porous film and a supporting member with holes, in which the supporting member is laminated on the porous film, and a partially enlarged view of a cavity having a cell adhesive region formed thereon.

FIG. 1 is a perspective view showing an embodiment of a tissue construct-forming kit having a tissue construct-forming substrate prepared by this preparation step. This tissue construct-forming kit is provided with a tissue construct-forming substrate having cell adhesive regions 3a on a porous film surface 2 mentioned below and a frame-shaped supporting member 5a that supports the periphery of the substrate. FIG. 2 is a perspective view showing another embodiment of a tissue construct-forming kit having a tissue construct-forming substrate prepared by this preparation step. This tissue construct-forming kit comprises a tissue construct-forming substrate having cell adhesive regions 3a on a porous film surface 2 mentioned below and a plate-shaped supporting member 5b laminated and fixed on the tissue construct-forming substrate. The plate-shaped supporting member 5b has through-holes spaced a predetermined distance apart from one another and is formed such that the through-holes divide an area having cell adhesive regions 3a.

It is preferred that the tissue construct-forming kit of the invention includes at least a tissue construct-forming substrate composed of a porous film having small communicating holes, maintains this flexible porous film in a form suitable for use, and is in a mode of being supported by a supporting member for improving its handling property.

1. Supporting Member

The supporting member which is provided as needed in the substrate for forming a three-dimensional tissue construct of the invention is not limited in terms of its form as long as it functions as a member capable of fixing and supporting a porous film mentioned below and as a stable structural body. The supporting member may be, for example, a supporting member in the form of a frame 5a disposed in the periphery of a porous film 1 as shown in FIG. 1, or may be a lattice-shaped supporting member in which frame materials are mutually orthogonal while being spaced a predetermined distance apart from one another.

Further, it may not support the peripheral region like a frame. For example, as shown in FIG. 2, it may be in a plate shape which is stable as it is, and in a form in which a supporting member 5b having through-holes which are formed such that they are spaced a predetermined distance for placing each cell adhesive region mentioned below in the center is laminated and fixed on a surface 2 of a porous film 1.

The material of this substrate is not particularly limited, and for example, it can be formed of glass, a synthetic resin, a synthetic rubber such as EPDM (ethylene propylene diene monomer), natural rubber, a ceramic, stainless steel and the like. As the synthetic resin, for example, polystyrene, polyethylene, polypropylene, polycarbonate, polyamide, polyacetal, a polyester (such as polyethylene terephthalate), polyurethane, polysulfone, polyacrylate, polymethacrylate, polyvinyl, silicone and the like can be preferably used.

2. Porous Film

A porous film to be used in the tissue construct-forming substrate of the invention, or, the "porous film having through-holes" in the invention refers to a film having through-holes or communicating holes which serve as transmission paths for transferring a substance in either or both of the transfer of substances between the front and back surfaces of the film, and between the different types of regions such as a cell adhesive region and a cell non-adhesive region on the surface of the film. The substrate film is not particularly limited in terms of its material or structure, the form or size of the hole, hole size distribution, hole position distribution, and hole area ratio (a ratio of the total area of holes on the surface to the total area of the film), and any film can be used as long as it is a film having such through-holes (including the case of communicating holes) and capable of retaining a tissue construct of cells or the like on the surface. As more specific examples, those satisfying the following conditions can be exemplified.

In the invention, the relationship between the cell adhesive region and the cell non-adhesive region, which is a peripheral region thereof, is sometimes referred to as "different types of regions".

As for the material, for example, it can be formed of glass, a synthetic resin, a synthetic rubber such as EPDM (ethylene propylene diene monomer), natural rubber, a ceramic, stainless steel or the like. As the synthetic resin, for example, polystyrene, polyethylene, polypropylene, polycarbonate, polyamide, polyacetal, a polyester (such as polyethylene terephthalate), polyurethane, polysulfone, polyacrylate, polymethacrylate, polyvinyl, silicone or the like can be preferably used.

As for the structure, for example, a so-called porous organic resin film, an inorganic porous film composed of an inorganic material such as a ceramic, a mesh film, a microfabricated film produced by a given method and the like can be exemplified.

Examples of the microfabricated film include a porous film in which holes with a given size, shape, distribution and pattern (for example, a film in which uniform hexagonal columnar holes with a size of 10 μm are arranged in a honeycomb pattern, a film in which random cylindrical columnar holes with an average diameter of from 1 μm to 10 μm are arranged randomly or the like) are formed using a photolithography technique, a porous film produced in a similar manner by micropunching or injection molding and the like.

As for the form and size of the hole, for example, a porous structure having through-holes in the form of a cylindrical column or a square column with a size not larger than 80% of the average size of cells or holes which have a size smaller than the average size of cells and communicate with the front and back surfaces, and the like can be exemplified.

As for the hole size distribution or hole position distribution, for example, a filter with monodisperse holes such as a fine mesh filter, and a filter with polydisperse holes such as a general porous film can be exemplified.

As for the hole area ratio, a filter with a hole area ratio exceeding 80% such as a fine mesh filter, a filter with a hole area ratio not more than 50% such as a general porous film, or the like can be used according to the intended purpose.

It is preferred that the hole size of a porous film which can be used in the invention is a hole size not larger than 80% of the average size of cells or smaller than the average size of cells as described above for forming a three-dimensional tissue construct. More specifically, the hole size is preferably in the range of from 0.01 μm to 100 μm, more preferably from 0.1 μm to 50 μm, further more preferably from 1 μm to 20 μm. The size of the holes of the porous film in the present invention indicates the maximum diameter of the holes regardless of the shape thereof. For example, it indicates the length of the diameter for a circular hole and the length of the diagonal for a rectangular hole.

The size of the holes in this porous film can be measured by surface observation using a commercially available high-powered microscope or SEM.

As will be described in detail below, by controlling the relationship between the average size of cells to be cultured and the hole size, it becomes possible to form a tissue construct not only on the front surface of the porous film but also on the back surface opposite to the inoculated side, for instance.

Figure 14A:
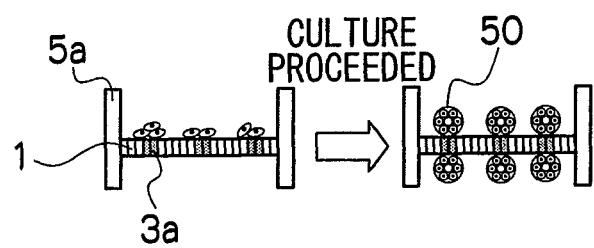
FIGS. 14A and 14B are schematic views showing a state of forming assemblies formed in Example 6.
Figure 14B:
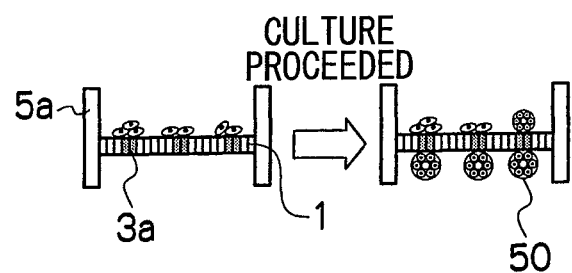

That is, as shown in the schematic view of FIG. 14A, in the case where a film with a hole size smaller than the size of cells is used as the porous film 1, a tissue construct 50 can be formed on both surfaces, i.e., the porous film surface 2 on the side inoculated with cells and the porous film surface (back surface) opposite to the side inoculated with cells. On the other hand, in the case where culture is carried out in a similar manner using a film with a hole size larger than the size of cells is used as the porous film 1, a tissue construct 50 is formed not on the porous film surface 2 on the side inoculated with cells, but on the back surface of the porous film opposite to the side inoculated with cells as shown in FIG. 14B. Accordingly, it was revealed by the investigation made by the present inventors that by controlling the hole size of the porous film, the direction of formation of tissue construct can be controlled.

As the method for producing the porous film, a method in which a sheet-shaped woven material is produced by knitting or weaving a wire-shaped or filamentous material at a high density, a method in which a non-woven cloth is produced by forming a fiber mass through entanglement or fusion of fiber or using a binder or the like, a method in which a porous film or a porous sheet is produced by forming a communicating hole structure using a resin material or the like through foaming, press-foaming or the like, a method in which a film having communicating holes or through-holes formed thereon by a casting method, in which a liquid containing an organic solvent and a polymeric compound is casted on a support, is formed, a method in which a porous film is obtained through perforation employing a method such as punching, and the like can be exemplified.

Among the above-mentioned porous films, the most preferred is a porous film having communicating holes in a honeycomb form or any form formed therein obtained through film formation by casting a liquid containing an organic solvent and a polymeric compound on a support thereby to form voids in the film.

A film having communicating holes is obtained by applying such a casting method and adjusting respective conditions including raw materials such as a resin base material, a solvent and an additive, the humidity in a film-forming atmosphere, a supplying condition for humid air and the like. This embodiment is preferable from the viewpoint of simplicity of the process because the formed holes not only function as through-holes but also communicate with other peripheral holes present adjacent at a position parallel to the direction of formation of the film, whereby a porous film having voids as a so-called three-dimensional network structure can be supplied without using a complicated process. It is advantageous that the porous film to be used in the invention has holes communicating not only in the vertical direction (thickness direction) of the film but also in the planar direction from the viewpoint of material exchange such as supply of oxygen and a culture medium to cultured cells and discharge of waste product and the like.

Hereinafter, the porous film having three-dimensionally communicating holes (hereinafter appropriately referred to as a specific porous film), which is the most preferred embodiment, will be described.

A Specific Porous Film

A material to be used for forming a porous film such as the above-mentioned porous film having three-dimensionally communicating holes is not particularly limited, and can be appropriately selected according to the intended purpose. Specifically, for example, at least one member selected from a group consisting of hydrophobic polymers and amphiphilic compounds is preferred.

The hydrophobic polymer constituting a porous film can be appropriately selected according to the intended purpose from known polymers, and examples thereof include vinyl-type polymers (for example, polyethylene, polypropylene, polystyrene, polyacrylate, polymethacrylate, polyacrylamide, polymethacrylamide, polyvinyl chloride, polyvinylidene chloride, polyvinylidene fluoride, polyhexafluoropropene, polyvinyl ethers, polyvinyl carbazole, polyvinyl acetate, polytetrafluoroethylene and the like), polyesters (for example, polyethylene terephthalate, polyethylene naphthalate, polyethylene succinate, polybutylene succinate, polylactate and the like), polylactones (for example, polycaprolactone and the like), polyamides and polyimides (for example, nylon, polyamic acid and the like), polyurethane, polyurea, polycarbonate, polyaromatics, polysulfone, polyethersulfone, polysiloxane derivatives and the like. These may be used as a homo polymer, a copolymer obtained by copolymerization of two or more structural units, or a polymer blend which is a mixture of two or more polymers as needed, in view of solubility, optical physical properties, electric physical properties, film strength, elasticity and the like.

The amphiphilic compound to be used for forming a porous film is not particularly limited, and can be appropriately selected according to the intended purpose. Examples of the amphiphilic compound include amphiphilic polymers.

The amphiphilic polymer can be appropriately selected according to the intended purpose, and examples thereof include an amphiphilic polymer having polyacrylamide as a main backbone chain, a dodecyl group as a hydrophobic side chain and a carboxyl group as a hydrophilic side chain, a polyethylene glycol/polypropylene glycol block copolymer and the like.

The hydrophobic side chain is a nonpolar linear group such as an alkylene group or a phenylene group and preferably has no hydrophilic group such as a polar group or an ionic dissociation group as a pendant until the terminal except for a linking group such as an ester group or an amide group. For example, the hydrophobic side chain is preferably composed of five or more methylene units when the alkylene group is used.

The hydrophilic side chain preferably has a structure having a hydrophilic moiety such as a polar group, an ionic dissociation group or an oxyethylene group in the terminal through a linking moiety such as an alkylene group.

Compounds other than amphiphilic polymers can also be exemplified as the amphiphilic compounds. The amphiphilic compounds other than the amphiphilic polymers can be appropriately selected according to the intended purpose. For example, surfactants and the like are preferred.

As the surfactant to be used as the amphiphilic compound, for example, a compound represented by the following general formula (I) and the like are exemplified.

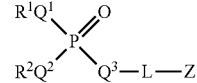

General formula (I)

In the general formula (I), $R^1$ represents an aliphatic group, an alicyclic compound group, an aromatic group or a heterocyclic ring, and $R^2$ represents an aliphatic group, an alicyclic compound group, an aromatic group, a heterocyclic ring or -L-Z. $Q^1$, $Q^2$ and $Q^3$ each represent a single bond, an oxygen atom, a sulfur atom or $—N(R^3)—$, and $R^3$ represents a hydrogen atom, an aliphatic group, an alicyclic compound group, an aromatic group, a heterocyclic ring or -L-Z. L represents a divalent linking group, and Z represents an ionic group. The single bond means that no element is present. For example, when $Q^1$ represents a single bond, P is directly linked to $R^1$.

In the general formula (I), as the aliphatic group represented by $R^1$, for example, a linear or branched unsubstituted alkyl group having 1 to 40 carbon atoms, a linear or branched substituted alkyl group having 1 to 40 carbon atoms, a linear or branched unsubstituted alkenyl group having 2 to 40 carbon atoms, a linear or branched substituted alkenyl group having 2 to 40 carbon atoms, a linear or branched unsubstituted alkynyl group having 2 to 40 carbon atoms, a linear or branched substituted alkynyl group having 2 to 40 carbon atoms and the like are preferred.

Examples of the linear or branched unsubstituted alkyl group having 1 to 40 carbon atoms include a methyl group, an ethyl group, an n-propyl group, an iso-propyl group, an n-butyl group, a sec-butyl group, a tert-butyl group, an n-amyl group, a tert-amyl group, an n-hexyl group, an n-heptyl group, an n-octyl group, a tert-octyl group, a 2-ethylhexyl group, an n-nonyl group, a 1,1,3-trimethylhexyl group, an n-decyl group, an n-dodecyl group, a cetyl group, a hexadecyl group, a 2-hexyldecyl group, an octadecyl group, an eicosyl group, a 2-octyldodecyl group, a docosyl group, a tetracosyl group, a 2-decyltetradecyl group, a tricosyl group and the like.

Examples of the substituent of the linear or branched substituted alkyl group having 1 to 40 carbon atoms include an alkoxyl group, an aryl group, a halogen atom, a carbon ester group, a carbon amide group, a carbamoyl group, an oxycarbonyl group, a phosphoric acid ester group and the like. Specific examples thereof include a benzyl group, a β-phenetyl group, a 2-methoxyethyl group, a 4-phenylbutyl group, a 4-acetoxyethyl group, a 6-phenoxyhexyl group, a 12-phenyldodecyl group, a 18-phenyloctadecyl group, a heptadecylfluorooctyl group, a 12-(p-chlorophenyl)dodecyl group, a 2-(diphenyl phosphate)ethyl group and the like.

Examples of the linear or branched unsubstituted alkenyl group having 2 to 40 carbon atoms include a vinyl group, an allyl group, a 3-butenyl group, a 2-methyl-2-butenyl group, a 4-pentenyl group, a 3-pentenyl group, a 3-methyl-3-pentenyl group, a 5-hexenyl group, a 4-hexenyl group, a 3-hexenyl group, a 2-hexenyl group, a 7-octenyl group, a 9-decenyl group, an oleyl group, a linoleyl group, a linolenyl group and the like.

Examples of the linear or branched substituted alkenyl group having 2 to 40 carbon atoms include a 2-phenylvinyl group, a 4-acetyl-2-butenyl group, a 13-methoxy-9-octadecenyl group, a 9,10-dibromo-12-octadecenyl group and the like.

Examples of the linear or branched unsubstituted alkynyl group having 2 to 40 carbon atoms include an acetylene group, a propargyl group, a 3-butynyl group, a 4-pentynyl group, a 5-hexynyl group, a 4-hexynyl group, a 3-hexynyl group, a 2-hexynyl group and the like.

Examples of the substituent of the linear or branched substituted alkynyl group having 2 to 40 carbon atoms include an alkoxyl group, an aryl group and the like. Specific examples thereof include a 2-phenylacetylene group, a 3-phenylpropargyl group and the like.

In the general formula (I), as the alicyclic compound group represented by $R^1$, for example, a substituted or unsubstituted cycloalkyl group having 3 to 40 carbon atoms, a substituted or unsubstituted cycloalkenyl group having 4 to 40 carbon atoms and the like are preferred.

As the aromatic group, for example, a substituted or unsubstituted aryl group having 6 to 50 carbon atoms and the like are preferred.

Examples of the substituted or unsubstituted cycloalkyl group having 3 to 40 carbon atoms as the alicyclic compound group include a cyclopropyl group, a cyclohexyl group, a 2,6-dimethylcyclohexyl group, a 4-tert-butylcyclohexyl group, a 4-phenylcyclohexyl group, a 3-methoxycyclohexyl group, a cycloheptyl group and the like.

Examples of the substituted or unsubstituted cycloalkenyl group having 4 to 40 carbon atoms as the alicyclic compound group include a 1-cyclohexenyl group, a 2-cyclohexenyl group, a 3-cyclohexenyl group, a 2,6-dimethyl-3-cyclohexenyl group, a 4-tert-butyl-2-cyclohexenyl group, a 2-cycloheptenyl group, a 3-methyl-3-cycloheptenyl group and the like.

Examples of the substituent of the substituted or unsubstituted aryl group having 6 to 50 carbon atoms as the aromatic group include an alkyl group, an alkoxyl group, an aryl group, a halogen atom and the like. Specific examples thereof include a phenyl group, a 1-naphthyl group, a 2-naphthyl group, an anthranyl group, an o-cresyl group, a m-cresyl group, a p-cresyl group, a p-ethylphenyl group, a p-tert-butylphenyl group, a 3,5-di-tert-butylphenyl group, a p-n-amylphenyl group, a p-tert-amylphenyl group, a 2,6-dimethyl-4-tert-butylphenyl group, a p-cyclohexylphenyl group, an octylphenyl group, a p-tert-octylphenyl group, a nonylphenyl group, a p-n-dodecylphenyl group, a m-methoxyphenyl group, a p-butoxyphenyl group, a m-octyloxyphenyl group, a biphenyl group, a m-chlorophenyl group, a pentachlorophenyl group, a 2-(5-methylnaphthyl) group and the like.

In the general formula (I), as the heterocyclic ring, for example, a substituted or unsubstituted cyclic ether having 4 to 40 carbon atoms, a substituted or unsubstituted nitrogen-containing ring having 4 to 40 carbon atoms and the like are preferred.

Examples of the substituted or unsubstituted cyclic ether having 4 to 40 carbon atoms include a furyl group, a 4-butyl-3-furyl group, a pyranyl group, a 5-octyl-2H-pyran-3-yl group, an isobenzofuranyl group, a chromenyl group and the like.

Examples of the substituted or unsubstituted nitrogen-containing ring having 4 to 40 carbon atoms include a 2H-pyrrolyl group, a pyrrolyl group, an imidazolyl group, a pyrazolyl group, an indolizinyl group, a morpholyl group and the like.

Among these, particularly preferred are a linear, cyclic or branched unsubstituted alkyl group having 1 to 24 carbon atoms, a linear, cyclic or branched substituted alkyl group having 1 to 24 carbon atoms exclusive of carbon atoms of the substituent, a linear, cyclic or branched unsubstituted alkenyl group having 2 to 24 carbon atoms, a linear, cyclic or branched substituted alkenyl group having 2 to 24 carbon atoms, and a substituted or unsubstituted aryl group having 6 to 30 carbon atoms.

Examples of the linear, cyclic or branched unsubstituted alkyl group having 1 to 24 carbon atoms include a methyl group, an ethyl group, an n-propyl group, an n-butyl group, an n-amyl group, an n-hexyl group, a cyclohexyl group, an n-heptyl group, an n-octyl group, a 2-ethylhexyl group, an n-nonyl group, a 1,1,3-trimethylhexyl group, an n-decyl group, an n-dodecyl group, a cetyl group, a hexadecyl group, a 2-hexyldecyl group, an octadecyl group, an eicosyl group, a 2-octyldodecyl group, a docosyl group, a tetracosyl group, a 2-decyltetradecyl group and the like.

Examples of the linear, cyclic or branched substituted alkyl group having 1 to 24 carbon atoms exclusive of carbon atoms of the substituent include a 6-phenoxyhexyl group, a 12-phenyldodecyl group, a 18-phenyloctadecyl group, a heptadecylfluorooctyl group, a 12-(p-chlorophenyl)dodecyl group, a 4-tert-butylcyclohexyl group and the like.

Examples of the linear, cyclic or branched unsubstituted alkenyl group having 2 to 24 carbon atoms include a vinyl group, an allyl group, a 2-methyl-2-butenyl group, a 4-pentenyl group, a 5-hexenyl group, a 3-hexenyl group, a 3-cyclohexenyl group, a 7-octenyl group, a 9-decenyl group, an oleyl group, a linoleyl group, a linolenyl group and the like.

Examples of the linear, cyclic or branched substituted alkenyl group having 2 to 24 carbon atoms include a 2-phenylvinyl group, a 9,10-dibromo-12-octadecenyl group and the like.

Examples of the substituted or unsubstituted aryl group having 6 to 30 carbon atoms include a phenyl group, a 1-naphthyl group, a 2-naphthyl group, a p-cresyl group, a p-ethylphenyl group, a p-tert-butylphenyl group, a p-tert-amylphenyl group, an octylphenyl group, a p-tert-octylphenyl group, a nonylphenyl group, a p-n-dodecylphenyl group, a m-octyloxyphenyl group, a biphenyl group and the like.

In the general formula (I), as $Q^1$, $Q^2$ and $Q^3$, a single bond, an oxygen atom or —$N(R^3)$—, is preferred, and it is particularly preferred that at least two or more of $Q^1$, $Q^2$ and $Q^3$ are an oxygen atom.

In the general formula (I), as L, a group represented by the following general formula (II) is preferred.

General formula (II)

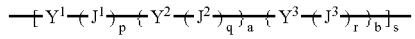

In the general formula (II), $Y^1$, $Y^2$ and $Y^3$ may be the same or different, and each represents a substituted or unsubstituted alkylene group having 1 to 40 carbon atoms or a substituted or unsubstituted arylene group having 6 to 40 carbon atoms. $J^1$, $J^2$ and $J^3$ may be the same or different, and each represents a divalent linking unit. p, q and r each independently represent an integer of 0 to 5. s represents an integer of 1 to 10. a and b each independently represent an integer of 0 to 50.

Examples of the substituent of $Y^1$, $Y^2$ and $Y^3$ include the groups described above as the examples of the substituent of $R^1$ in the general formula (I). Specifically, for example, as the alkylene group, a methylene group, an ethylene group, a propylene group, a trimethylene group, a tetramethylene group, a pentamethylene group, a hexamethylene group, a 1,4-cyclohexylene group, an octamethylene group, a decamethylene group, 2-methoxy-1,3-propylene group and the like are preferred, and as the arylene group, an o-phenylene group, a m-phenylene group, a p-phenylene group, a 3-chloro-1,4-phenylene group, a 1,4-naphthylene group, a 1,5-naphthylene group and the like are preferred. Among these, particularly preferred are an ethylene group, a propylene group, a trimethylene group, a tetramethylene group, a pentamethylene group, a hexamethylene group, a 1,4-cyclohexylene group, an octamethylene group, a decamethylene group, a m-phenylene group and a p-phenylene group.

As the divalent linking unit represented by each of the above-mentioned $J^1$, $J^2$ and $J^3$, for example, a single bond, —O—, —S—, —CO—, —COO—, —OCO—, —CON($R^4$)—, —N($R^4$)CO—, —CON($R^4$)CO—, —N($R^4$)CON($R^5$)—, —OCON($R^4$)—, —N($R^4$)COO—, —$SO_2$—, —$SO_2$N($R^4$)—, —N($R^4$)$SO_2$—, —N(COR$^4$)—, —OP(=O)(OR$^1$)O— and the like are preferred. Incidentally, $R^1$ represents the same meaning as in the general formula (I), $R^4$ represents a hydrogen atom, an unsubstituted alkyl group having 1 to 6 carbon atoms or a substituted alkyl group having 1 to 6 carbon atoms exclusive of carbon atoms of the substituent, and $R^5$ represents the same meaning as $R^4$, however, $R^4$ and $R^5$ may be the same or different.

Examples of the substituent of $R^4$ and $R^5$ include an aryl group, an alkoxyl group, a halogen atom and the like.

Among these, a single bond, —O—, —S—, —CO—, —COO—, —OCO—, —CON($R^{41}$)— (wherein $R^{41}$ represents a hydrogen atom, a methyl group, an ethyl group or a propyl group), —N($R^4$)CO—, —$SO_2$N($R^4$)—, —N($R^4$)$SO_2$— and the like are particularly preferred.

The above-mentioned p, q and r each independently are preferably an integer of 0 to 3, and particularly preferably an integer of 0 or 1.

The above-mentioned s is preferably an integer of 1 to 5, and particularly preferably an integer of 1 to 3. The above-mentioned a and b each independently are preferably an integer of 0 to 20, and particularly preferably an integer of 0 to 10.

In the general formula (I), Z is preferably a hydrophilic anionic or cationic ionic group and particularly preferably an anionic group.

As the anionic group, —COOM, —$SO_3$M, —$OSO_3$M, —PO(OM)$_2$, —OPO(OM)$_2$ are particularly preferred. Incidentally, M represents a counter cation, and is preferably an alkali metal ion (for example, lithium ion, sodium ion, potassium ion or the like), an alkaline earth metal ion (for example, magnesium ion, calcium ion or the like) or an ammonium ion. Among these, particularly preferred are sodium ion and potassium ion.

Examples of the cationic group include —$NH_3^+$.$X^-$, —$NH_2(R)^+$.$X^-$, —$NH(R^6)_2^+$.$X^-$, and —$N(R^6)_3^+$.$X^-$.

The above-mentioned $R^6$ represents an alkyl group having 1 to 3 carbon atoms (for example, a methyl group, an ethyl group, a 2-hydroxyethyl group, an n-propyl group, an isopropyl group or the like), and a methyl group and a 2-hydroxyethyl group are preferred.

The above-mentioned $X^-$ represents a counter anion, and for example, a halogen ion (for example, fluoride ion, chloride ion, bromide ion or the like), a complex inorganic anion (for example, hydroxide ion, sulfate ion, nitrate ion, phosphate ion or the like) and an organic compound anion (for example, oxalate ion, formate ion, acetate ion, propionate ion, methanesulfate ion, p-toluenesulfonate ion or the like) are preferred, and chloride ion, sulfate ion, nitrate ion or acetate ion are particularly preferred.

In the general formula (I), as $R^2$, a monovalent group selected from the groups described above as the examples of $R^1$ and groups described above as the examples of -L-Z. In the case where it is selected from the groups described above as the examples of $R^1$, it may have the same structure as or a different structure from that of $R^1$ present in the same molecule. Further, also in the case where it is selected from the groups described above as the examples of -L-Z, it may have the same structure as or a different structure from that of -L-Z present in the same molecule. $R^2$ is particularly preferably selected from the groups described above as the examples of $R^1$. The total number of carbon atoms present in $R^1$ and $R^2$ is preferably 6 or more and 80 or less, particularly preferably 8 or more and 50 or less.

As specific examples of the surfactant, illustrative compounds (PW-1) to (PW-52) will be shown below, however, the invention is not limited to these specific examples.

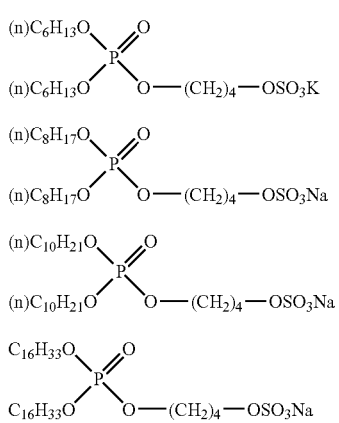

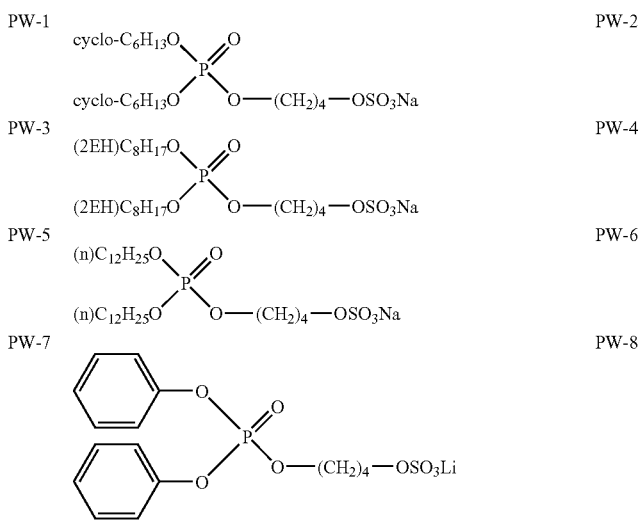

-continued
PW-9
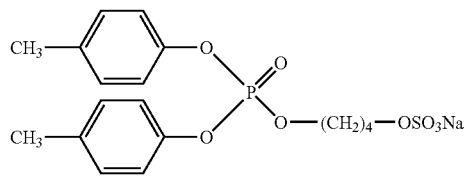
PW-10
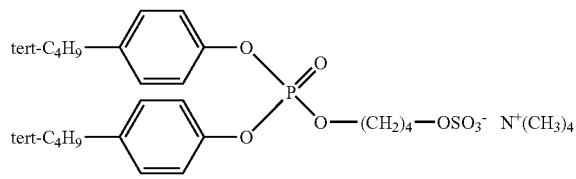
PW-11
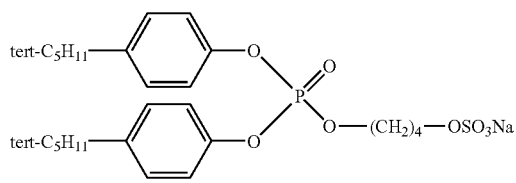
PW-12
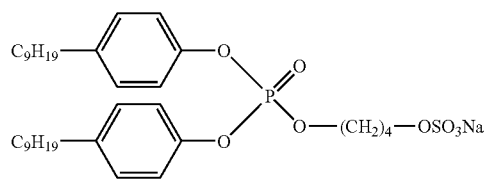
PW-13
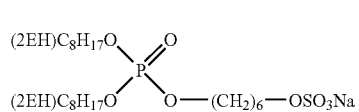
PW-14
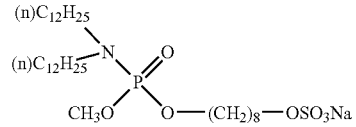
PW-15
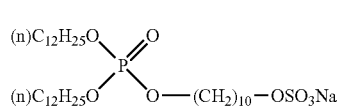
PW-16
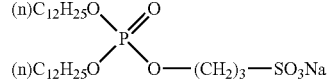
PW-17
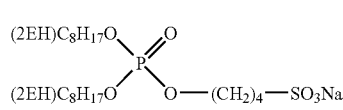
PW-18
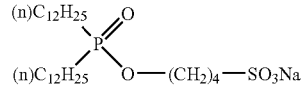
PW-19
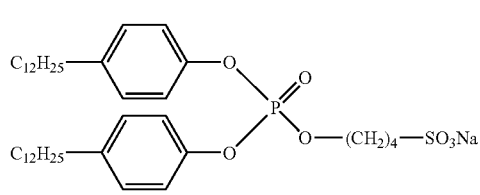
PW-20
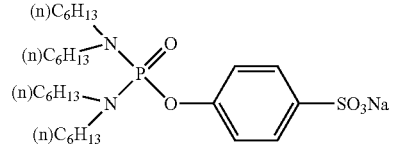
PW-21
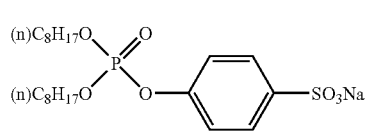
PW-22
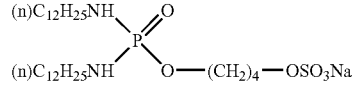
PW-23
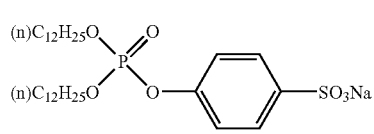
PW-24
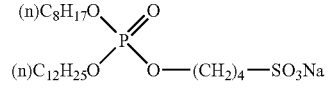
PW-25
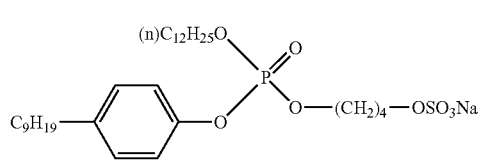
PW-26
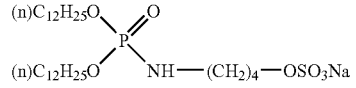
PW-27
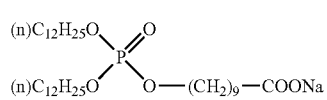
PW-28
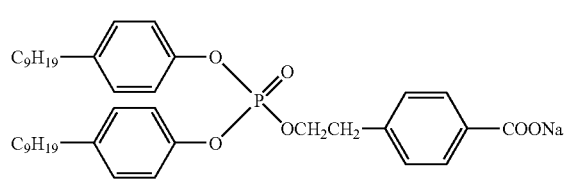

-continued
PW-29 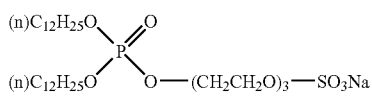
PW-30 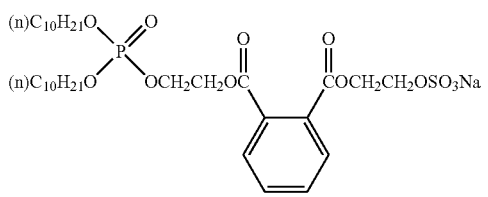
PW-31 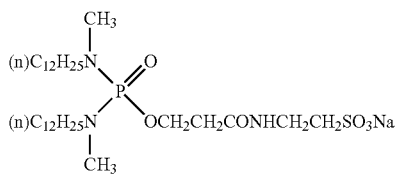
PW-32 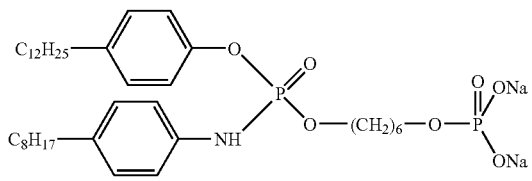
PW-33 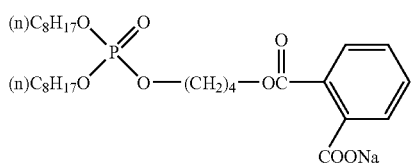
PW-34 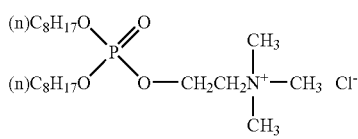
PW-35 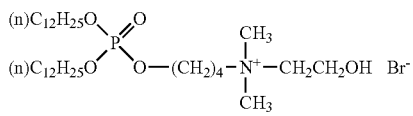
PW-36 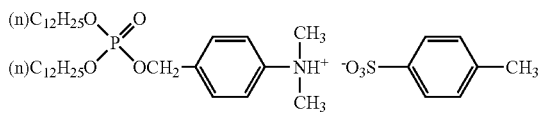
PW-37 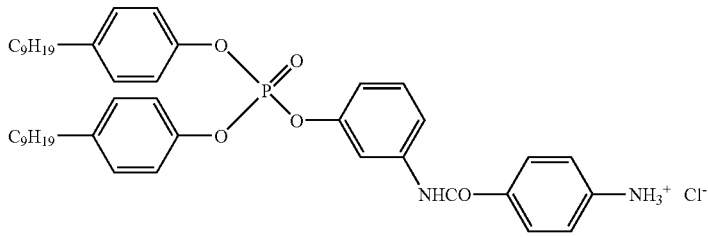
PW-38 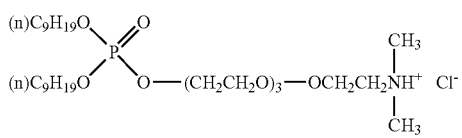
PW-39 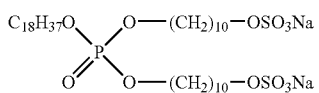
PW-40 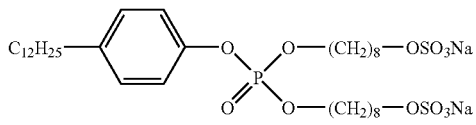
PW-41 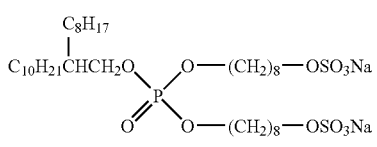
PW-42 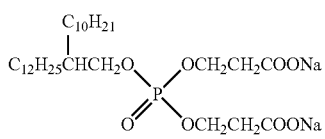
PW-43 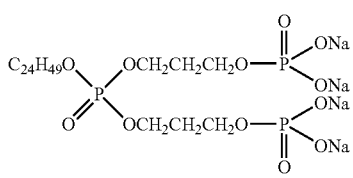
PW-44 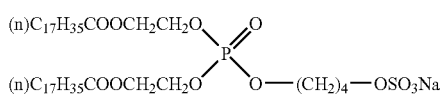
PW-45 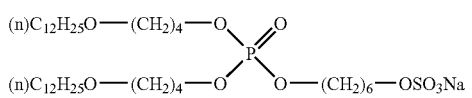

-continued

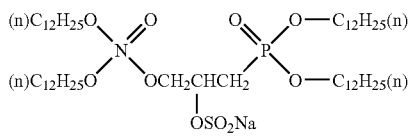
PW-46

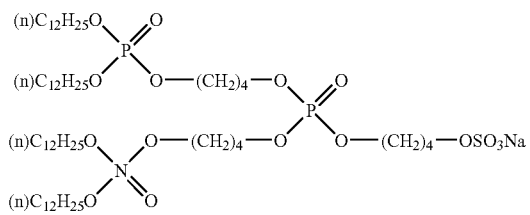
PW-47

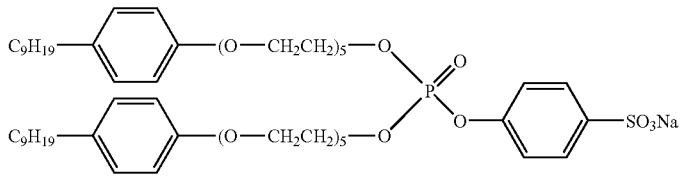
PW-48

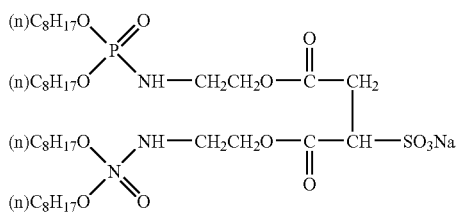
PW-49

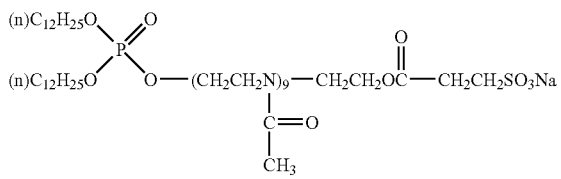
PW-50

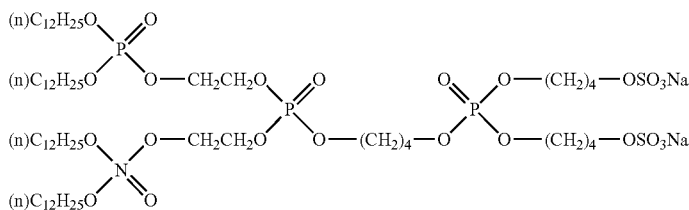
PW-51

PW-52

Although the ratio of the hydrophobic side chain to the hydrophilic side chain varies depending on the size or nonpolarity of molecule, the intensity of polarity, the strength of hydrophobicity of a hydrophobic organic solvent or the like and cannot be specified in general, the unit ratio (hydrophobic side chain/hydrophilic side chain) is preferably in the range of from 9.9/0.1 to 5.5/4.5. Further, in the case of a copolymer, it is more preferably a block copolymer in which a hydrophobic side chain and a hydrophilic side chain form a block such that the solubility thereof in a hydrophobic solvent is not affected than an alternating copolymer of a hydrophobic side chain and a hydrophilic side chain.

The weight average molecular weight (Mw) of a hydrophobic polymer and an amphiphilic polymer to be raw materials of a porous film is preferably in the range of from 10,000 to 10,000,000, more preferably from 50,000 to 1,000,000. As this weight average molecular weight, a value determined by the GPC method is adopted.

Further, in the case where the amphiphilic compound is a compound with a low molecular weight such as a surfactant, the molecular weight of the compound is preferably in the range of from 300 to 600.

When the specific porous film of the invention is formed, although only a hydrophobic polymer may be used as a raw material, it is preferred to use a hydrophobic polymer and an amphiphilic compound in combination.

In the case where the amphiphilic compound is an amphiphilic polymer, the compounding ratio (mass ratio) of the hydrophobic polymer to the amphiphilic compound is preferably in the range of from 99.9:0.1 to 50:50, and more preferably from 95:5 to 75:25. When the ratio of the amphiphilic compound falls within the above range, a uniform continuous porous structural body can be obtained, and also the stability, particularly the mechanical stability of the film can be sufficiently obtained.

Further, in the case where the amphiphilic compound is not an amphiphilic polymer, the compounding ratio (mass ratio) of the hydrophobic polymer to the amphiphilic compound is preferably in the range of from 99.9:0.1 to 80:20. In the case where the amphiphilic compound is an amphiphilic compound with a low molecular weight, a uniform continuous porous structural body can be obtained, and the film strength can be appropriately maintained within this compounding ratio.

As the amphiphilic compound, an amphiphilic polymer and an amphiphilic compound with a low molecular weight can be mixed at a given ratio and used.

It is also a preferred embodiment that the hydrophobic polymer and the amphiphilic polymer to be used as raw materials of a porous film are a polymerizable (crosslinkable) polymer having a polymerizable group in its molecule. Further, it is preferred that together with the hydrophobic polymer and/or the amphiphilic polymer, a polymerizable polyfunctional monomer is blended, and a porous structural body with communicating holes using the resulting mixture, followed by performing a curing treatment by a known method such as a thermal curing method, a UV curing method or an electron beam curing method from the viewpoint of improvement of strength of the porous film.

As the polyfunctional monomer that can be used with the hydrophobic polymer and/or the amphiphilic polymer, a polyfunctional (meth)acrylate is preferred from the viewpoint of reactivity. As the polyfunctional (meth)acrylate, for example, dipentaerythritol pentaacrylate, dipentaerythritol hexaacrylate, dipentaerythritol caprolactone adduct hexaacrylate or a modified compound thereof, an epoxy acrylate oligomer, a polyester acrylate oligomer, a urethane acrylate oligomer, N-vinyl-2-pyrrolidone, tripropylene glycol diacrylate, polyethylene glycol diacrylate, trimethylolpropane triacrylate, pentaerythritol triacrylate, pentaerythritol tetraacrylate or a modified compound thereof or the like can be used.

These polyfunctional monomers are used alone or in combination of two or more types thereof from the viewpoint of the balance between resistance to abrasion and flexibility.

In the case where the hydrophobic polymer and the amphiphilic polymer are a polymerizable (crosslinkable) polymer having a polymerizable group in its molecule, it is also preferred to use a polymerizable polyfunctional monomer that can react with the polymerizable group of the hydrophobic polymer and the amphiphilic polymer in combination.

In the present invention, a porous film having through-holes can be produced by forming a film under the conditions shown below by a casting method using such a substrate film.

In such a case where a film is formed by a casting method, with regard to the arrangement manner of holes, the holes are regularly arranged such that they are positioned in a hexagonal manner from a planar view thereby to form a honeycomb structure. Further, in the case where the holes adjacent to each other are closer than a predetermined distance, they are sometimes conjugated to communicate with each other.

The size of the hole varies depending on the type or amount of the solvent, hydrophobic polymer or amphiphilic compound used, and can be controlled mainly by the humidity in a casting atmosphere, and a timing of supplying humid air. In the film formation by the casting method in the invention, a water droplet generated by condensation with decreasing the temperature of environmental air due to vaporization heat of a casting liquid can be used as a template. For example, the size of condensed water droplet can be increased by relatively increasing the humidity, and consequently the size of the hole after film formation can be increased. Further, the growth of condensed water droplet proceeds using humid air as a supply source of water molecules until the solvent evaporates, therefore, by prolonging the time of supplying humid air, the size of condensed water droplet can be increased, and consequently the size of the hole after film formation can be increased. Specifically, in general, by controlling the humidity to be in the range of from 60 to 95% RH and the time of supplying humid air until drying to be in the range of from 1 to 5 min, the size of the hole can be controlled to be in the range of from 1 μm to 30 μm. In order to utilize the characteristic of the through-type structure, a condition for promoting accumulation of condensed water droplets is effective, although the condition varies depending on the type or amount of the solvent, hydrophobic polymer or amphiphilic compound to be used. Specifically, it is effective to promote the convection by decreasing the viscosity of casting liquid by selecting the hydrophobic polymer concentration or solvent, increasing the airflow for drying to such an extent that the cast surface is not disrupted, or humidifying the substrate.

More specifically, the viscosity of casting liquid is set to 0.1 Pa·s or less, the airflow for drying is set to 0.05 m/sec to 0.3 m/sec in the vertical direction with respect to the cast surface, and the substrate temperature is kept to be higher by 1 to 10° C. than the surface temperature of casting liquid (it can be measured using a commercially available radiation thermometer), whereby a porous film with a through-hole structure which is preferred in the invention can be formed.

3. Formation of Cell Adhesive Region

Next, a method for forming cell adhesive regions on a surface of the porous film is described.

A surface 2 of a porous film 1 shown in FIG. 1 has cell adhesive regions 3a. In the present specification, the cell adhesive regions 3a refer to regions having an affinity for cells to be cultured, and by forming such cell adhesive regions 3a, for example, in a solution such as a culture medium, cells sedimented on the cell adhesive regions 3a result in adhering to the regions 3a while their form changes from a spherical shape to a relatively flat shape with the lapse of culture time.

Specifically, in order to form such cell adhesive regions 3a, regions showing a charged state or hydrophilicity or hydrophobicity which enables cells to adhere to the regions in a solution such as a culture medium may be formed on the surface 2 of the porous film 1. More specifically, by fixing a cell adhesive substance obtained from a living body, or a synthesized cell adhesive substance or a derivative thereof is fixed on a predetermined region on the surface 2 of the porous film 1, the cell adhesive regions 3a can be formed.

As the cell adhesive substance to be used for forming the cell adhesive regions 3a, for example, a substance capable of binding to a specific molecule among cell surface molecules (for example, integrin, a receptor for a carbohydrate chain and the like) present on the cell membrane of cells to be cultured can be used. Specifically, as the cell adhesive substance obtained from the living body, for example, an extracellular matrix such as collagen, fibronectin or laminin can be preferably used.

Further, as the synthesized cell adhesive substance, for example, a compound having a specific amino acid sequence showing cell adhesiveness (for example, an Arg-Gly-Asp sequence (so-called RGD sequence) or the like) or a specific sugar-chain sequence showing cell adhesiveness (for example, a galactose side chain, or the like) can be preferably used.

As the derivative of such a cell adhesive substance, for example, a substance in which a given functional group, polymer chain or the like is bound to the cell adhesive substance by such as a given chemical reaction (for example, a condensation reaction between a carboxyl group and an amino group or the like) can be preferably used.

These cell adhesive substances or derivatives thereof can be fixed on a region of the porous film surface to form the cell adhesive regions 3a by contacting an aqueous solution containing the cell adhesive substance or a derivative thereof to the region followed by drying. In this way, any region can be converted into a cell adhesive region 3a. Further, these cell adhesive substances or derivatives thereof can also be fixed onto the region for forming the cell adhesive region 3a by, for example, binding a functional group of the cell adhesive substance or derivative thereof to a functional group which is exposed at each part of the porous film surface 2 at which a surface region 3a is to be formed, by a given chemical reaction (for example, a chemisorption reaction between a thiol group and a gold surface or the like, or a condensation reaction between a carboxyl group and an amino group) or the like in an aqueous solution containing the cell adhesive substance or a derivative thereof.

On the surface 2 of the porous film 1 shown in FIG. 1, a peripheral region of a plurality of cell adhesive regions 3a is a cell non-adhesive region (peripheral surface) 4a. That is, the periphery of the cell adhesive region 3a is surrounded by the cell non-adhesive region 4a, and an adjacent cell adhesive region 3a must be isolated by the cell non-adhesive region 4a. Here, the cell non-adhesive region 4a may be present as a continuous region.

FIG. 2 shows a tissue construct-forming substrate composed of a laminate of a plate-shaped substrate 5b having a plurality of through-holes with a predetermined depth and a porous film 1 at which the cell adhesive regions 3a are formed. This tissue construct-forming substrate is formed such that holes with a bottom (hereinafter referred to as "cavities 100"), of which the bottom surface is composed of the porous film, are arranged regularly. In a substantial center of the holes with a bottom, the cell adhesive region 3a is formed. The peripheral region of the cell adhesive region 3a is surrounded by the cell non-adhesive region 4b to form the bottom surface of the respective cavities 100. That is, apart from the cell adhesive regions 3a at the bottom surface shown in FIG. 2, the surface 2 of the porous film 1 consists of the cell non-adhesive region 4b, and the laminated plate-shaped substrate 5b itself is also has a cell non-adhesive surface which does not have any particular cell adhesiveness.

The cell non-adhesive surface is a surface exhibiting properties unsuitable for cell adhesion in, for example, an aqueous solution such as a culture medium. Therefore, in a culture medium, for example, the spherical shape of cells sedimented on the surface of the peripheral cell non-adhesive region 4a in FIG. 1, or the peripheral regions 4b of the cell adhesive regions 3a of the cavities (cell non-adhesive region) in FIG. 2 is hardly altered, and cannot substantially adhere to the peripheral surface 4a or the surface of the peripheral region 4b. That is, the cells sedimented on the peripheral surface 4a or the peripheral region 4b cannot adhere at all to the peripheral surface 4a or the surface region 4b and are suspended in the culture medium or, even if the cells adhere once thereto, they are easily released by the flow of the culture medium or the like after a predetermined culture time period has elapsed.

As the cell non-adhesive substance, for example, a substance that does not bind to cell surface molecules present on the cell membrane of cells to be cultured in the cell adhesive regions 3a can be used. Specifically, as a cell non-adhesive substance obtained from the living body, for example, a protein showing high hydrophilicity such as albumin or the like can be preferably used. Further, as a synthesized cell non-adhesive substance, for example, a compound containing a polymer chain showing extremely high hydrophilicity such as polyethylene glycol, MPC (2-methacryloyloxyethyl phosphorylcholine), poly-HEMA (polyhydroxyethyl methacrylate), SPC (segmented polyurethane) or the like can be preferably used. Further, as a derivative of such a cell non-adhesive substance, for example, a substance in which a given functional group, polymer chain or the like is bound to the cell non-adhesive substance by a given chemical reaction or the like can be preferably used.

Such a cell non-adhesive substance or a derivative thereof can be fixed on a region 4a surrounding the cell adhesive regions 3a in the surface 2 of the porous film shown in FIG. 1 or the peripheral regions 4b and the surface of the frame 5b shown in FIG. 2 using an aqueous solution containing the cell non-adhesive substance or a derivative thereof.

The cell non-adhesive substance or a derivative thereof can be fixed on the region (4a) surrounding the cell adhesive regions 3a shown in FIG. 1 or the respective peripheral regions 4b and the surface of the frame 5b shown in FIG. 2 by, for example, binding a functional group of the cell non-adhesive substance or a derivative thereof to a functional group exposed on the region (4a) surrounding the cell adhesive regions 3a in the surface 2 of the porous film shown in FIG. 1 or the respective cell non-adhesive regions 4b and the surface of the peripheral frame 5b shown in FIG. 2 by a given chemical reaction or the like in an aqueous solution containing the cell non-adhesive substance or a derivative thereof.

Further, the cavities 100 formed in the plate-shaped substrate (supporting member) 5b having through-holes shown in FIG. 2 can be formed using a known processing method which is selected according to the property of the material of the supporting member 5b or the like. Specifically, for example, such cavities 100 can be formed on the porous film surface 2 by a perforating process using a machining center or the like, an optical microfabrication process using a laser or the like, an etching process, an embossing process or the like, or they can be formed at the time of molding the substrate 5b by injection molding, press molding, stereolithography or the like.

By such a processing method, the cavities 100 can be formed as through-holes on, for example, the surface 2 of the substrate 5b with a predetermined thickness. Further, the cavities 100 can be formed as holes with a bottom by, for example, forming holes passing through the substrate 5b and then gluing the porous film 1 to one surface of the substrate 5b to form a bottom surface.

The plurality of cavities 100 can also be regularly formed on the substrate 5b such that the distance between the centers of the bottom surfaces of the circles becomes a fixed distance as shown in FIG. 2 by using a machining center or the like that precisely controls the processing positions with, for example, a CAD (computer aided design) program.

The surface 2 shown in FIG. 1 becomes a substantially flat surface in whole including the respective cell adhesive regions 3a and the cell non-adhesive surface 4a which is a peripheral region thereof. That is, the cell adhesive regions 3a and the peripheral surface 4a are substantially flat surfaces, respectively, and also continue with one another such that the entire porous film surface 2 constitutes a substantially flat surface. In the present specification, the substantially flat surface refers to, for example, a surface whose unevenness (for example, a difference in the level between the cell adhesive regions 3a and the peripheral surface 4a) is small to such an extent that it is smaller than the thickness of one cell. Further, in the surface 2 of the porous film 1 shown in FIG. 2, the respective cell adhesive regions 3a and the peripheral cell non-adhesive regions 4b are also formed, respectively as a substantially flat surface.

Further, the area of each cell adhesive region 3a cannot be specified in general because it varies depending on the size, type or condition of cells to be cultured or the like, however, for example, it is preferably in the range of from 300 $\mu m^2$ to $1 \times 10^6$ $\mu m^2$, particularly preferably from 5000 $\mu m^2$ to $2 \times 10^5$ $\mu m^2$. That is, the size of the respective cell adhesive regions 3a shown in FIGS. 1 and 2 is preferably about 2 to 50 times, particularly preferably about 5 to 30 times the size of cells to be cultured in the cell adhesive regions 3a. This is because cells form a tissue construct by three-dimensionally aggregating on the respective cell adhesive regions 3a, therefore, the area of these regions defines the number of cells to be contained in the tissue construct. That is, by setting the area of the respective cell adhesive regions $3a$ to 300 µm² or to have a size not smaller than twice the size of cells, for example, a necessary number of cells for forming a tissue construct can be sufficiently adhered to the respective surface regions $3a$, and further a necessary number of cells can be retained on the respective cell adhesive regions $3a$. Further, by setting the area of the cell adhesive region $3a$ to $1\times10^6$ µm² or to have a size not larger than 50 times the size of cells, the size of a tissue construct to be formed in this region $3a$ can be properly maintained, and for example, an event that the cells contained in a deep part of the tissue construct die or lose their function because they cannot sufficiently receive nutrition or oxygen from a culture medium or the like outside the tissue construct can be prevented from occurring.

The depth of the cavities 100 in the plate-shaped substrate 5*b* having through-holes shown in FIG. 2, that is, the thickness of the plate-shaped substrate 5*b* is preferably about 1 to 200 times, particularly preferably 2 to 100 times the size of cells to be used. By setting the depth of the cavities 100 to not less than the above-mentioned lower limit, the cells can be prevented from spilling out from the cavities 100 and the cells can be surely retained on the cell adhesive regions $3a$. Further, because a tissue construct to be formed starting from cells retained on each of the surface regions $3a$ in the cavities 100 is present at a position close to the surface of the hole with a bottom formed in the tissue construct-forming substrate, by setting the depth thereof to not more than the above-mentioned upper limit, operations after the culture step, for example, the workability of observation, evaluation or collection becomes favorable.

Further, the porous film surface 2 has one specific surface region (hereinafter referred to as a "specific region"), which is a part of the cell adhesive regions $3a$, which is a minimum number of the cell adhesive regions $3a$ required for controlling the size of the tissue construct in the present method and a plurality of surface regions located around and adjacent to the specific region (hereinafter referred to as "adjacent regions").

In the present invention, on the porous film surface 2, only one cell adhesive region $3a$ surrounded by the cell non-adhesive region $4a$ may be present. Further, in view of the purposes of cell culture and formation of a three-dimensional tissue construct, or evaluation thereof, a plurality of cell adhesive regions $3a$ are preferably formed on the porous film surface, and from the viewpoint of efficiency of culture or evaluation, the plurality of cell adhesive regions $3a$ are preferably located at equal distances from one another.

Hereinafter, such regions composed of a plurality of cell adhesive regions $3a$ and the cell non-adhesive region $4a$ which is a peripheral region thereof are referred to as a region set. The plurality of adjacent cell adhesive regions $3a$ included in the region set are disposed such that the distance from the centroid point (the center point of a circle in a circular adjacent region, the intersection point of diagonal lines in a square adjacent region or the like) of the respective regions to the centroid point of the specific region included in the region set (hereinafter referred to as a "centroid distance") is equal to one another.

One of the features of the present method is that by changing the centroid distance of a region set included in the porous film surface 2 prepared in the preparation step, the size of a three-dimensional tissue construct containing proliferating cells to be formed in the specific region in the culture step can be controlled according to the centroid distance. That is, for example, by preparing the porous film surface 2 including a region set with a predetermined centroid distance in the preparation step, a tissue construct with a predetermined size defined by the centroid distance can be formed at least in the specific region in the region set in the culture step.

Specifically, for example, in the case where a first porous film surface including a region set in which the specific region and the respective adjacent regions are located at a first centroid distance apart from one another is prepared in the preparation step, a tissue construct with a first size according to the first centroid distance can be formed in the culture step. On the other hand, in the case where a second porous film surface including a region set in which the specific region and the respective adjacent regions are located at a second centroid distance, which is smaller than the first centroid distance, apart from one another is prepared in the preparation step, a tissue construct with a second size, which is smaller than the first size according to a proportion of the second centroid distance to the first centroid distance, can be formed in the culture step. Accordingly, for example, when a plurality of porous film surfaces, in which the respective centroid distances are changed in a stepwise manner according to a fixed rule, are prepared in the preparation step, constructs with a size which is changed in a stepwise manner among the plurality of porous film surfaces according to the fixed rule can be formed in the plurality of specific regions on the plurality of porous film surfaces in the culture step. Here, an example of a case where the centroid distance may be changed according to a fixed rule is a case where relative to the centroid distance in one porous film surface, the centroid distance of another porous film surface or a plurality of other porous film surfaces is changed by a predetermined length, by a predetermined magnification or according to a predetermined function.

In this way, according to the present method, for example, a tissue construct array chip in which a plurality of constructs with a desired size defined by the centroid distance are arranged regularly and at a high density can be obtained. Further, according to the present method, for example, screening for a centroid distance to be set for forming a tissue construct with a desired size can be carried out for each type of cells to be cultured.

The smallest distance between a peripheral region of the specific region and a peripheral region of each adjacent region (that is, for example, in the case of circular surface region $3a$ and surface region $3b$, the smallest distance between a circumferential region of the specific region and a circumferential region of each adjacent region) cannot be indicated in general because the size of cells to be cultured in the specific region and each adjacent region varies depending on the type or condition of the cells; however, it is preferably in the range of from 50 µm to 1000 µm, particularly preferably from 100 µm to 700 µm. This is because in the case where the smallest distance thereof is smaller than 50 µm, for example, sometimes fusion or crosslinking is caused between a tissue construct formed in the specific region and a tissue construct formed in the adjacent region, and a tissue construct obtained by adhering the plurality of assemblies to each other is formed, and therefore the size of the tissue construct may not be precisely controlled. Further, when the smallest distance is larger than 1000 µm, because the distance between a tissue construct formed in the specific region and a tissue construct formed in the adjacent region is large, for example, a tissue construct array in which a plurality of assemblies are arranged at a high density cannot be obtained.

Figure 3:
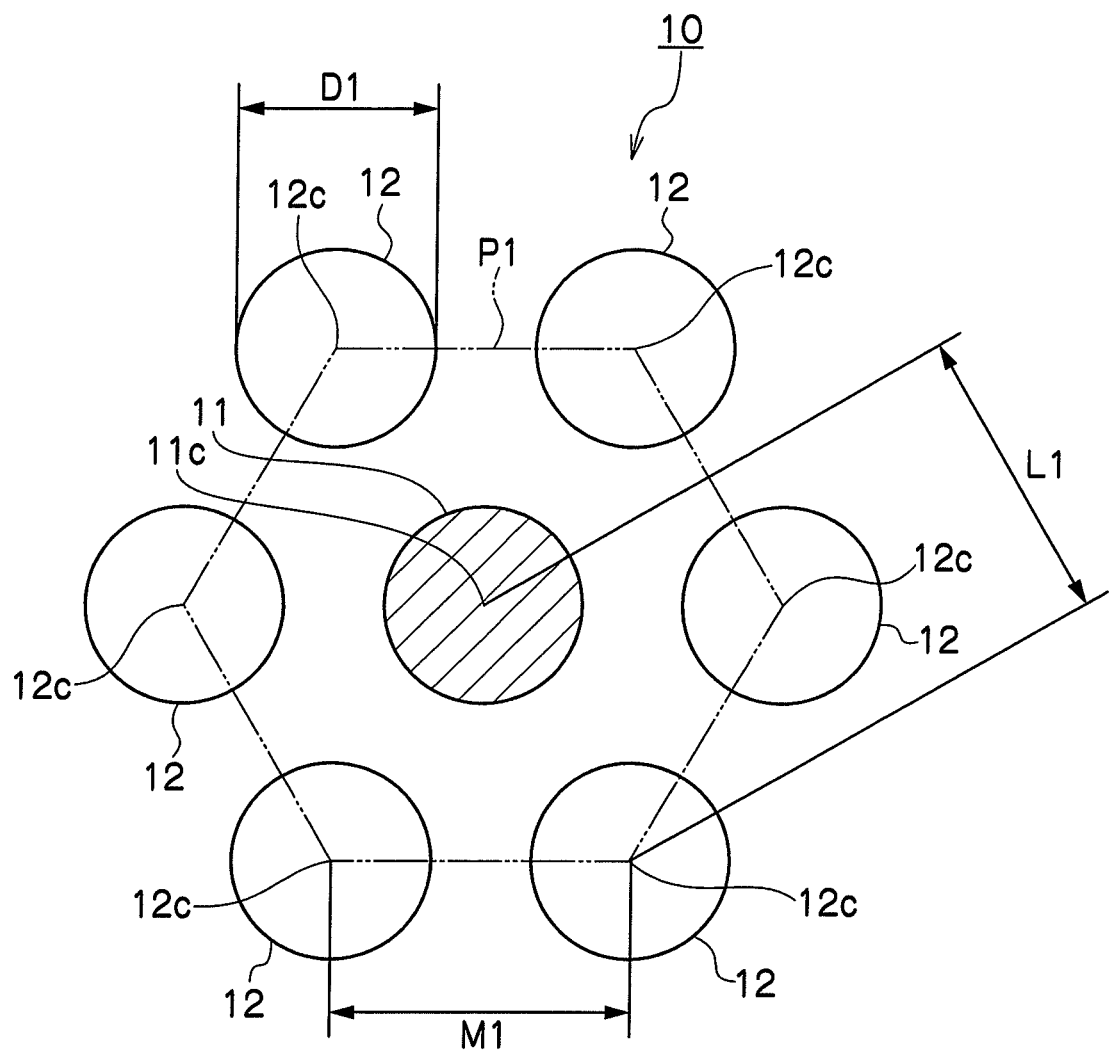
FIG. 3 is an explanatory view showing an example of a region set, which is used in a method for forming a tissue construct according to this embodiment.

FIG. 3 is an explanatory view of a region set 10 formed on the surface of the tissue construct-forming substrate shown in FIGS. 1 and 2.

This region set 10 has a specific region 11 (the hatched region in FIG. 3) which is one of the plurality of surface regions 3a (see FIGS. 1 and 2) formed on the porous film surface 2 and six adjacent regions 12 which are other part of the plurality of cell adhesive regions 3a or peripheral cell non-adhesive region 4a or 4b and are disposed such that they surround the specific region 11. The specific region 11 and the respective adjacent regions 12 are in the form of a circle with a diameter D1 equal to one another. Further, the distance between the center point 11c of the specific region 11 and the center point 12c of the respective adjacent regions 12 (hereinafter referred to as a "center distance") is a fixed value L1 equal to one another. Further, the specific region 11 is disposed such that its center point 11c coincides with the centroid point of the regular hexagon P1 formed by connecting the respective center points 12c of the six adjacent regions 12 and the entire specific region 11 is disposed in a regular hexagon P1. Further, in this region set 10, the length M1 of the respective six sides of the regular hexagon P1 is the same as the center distance L1.

Figure 4:
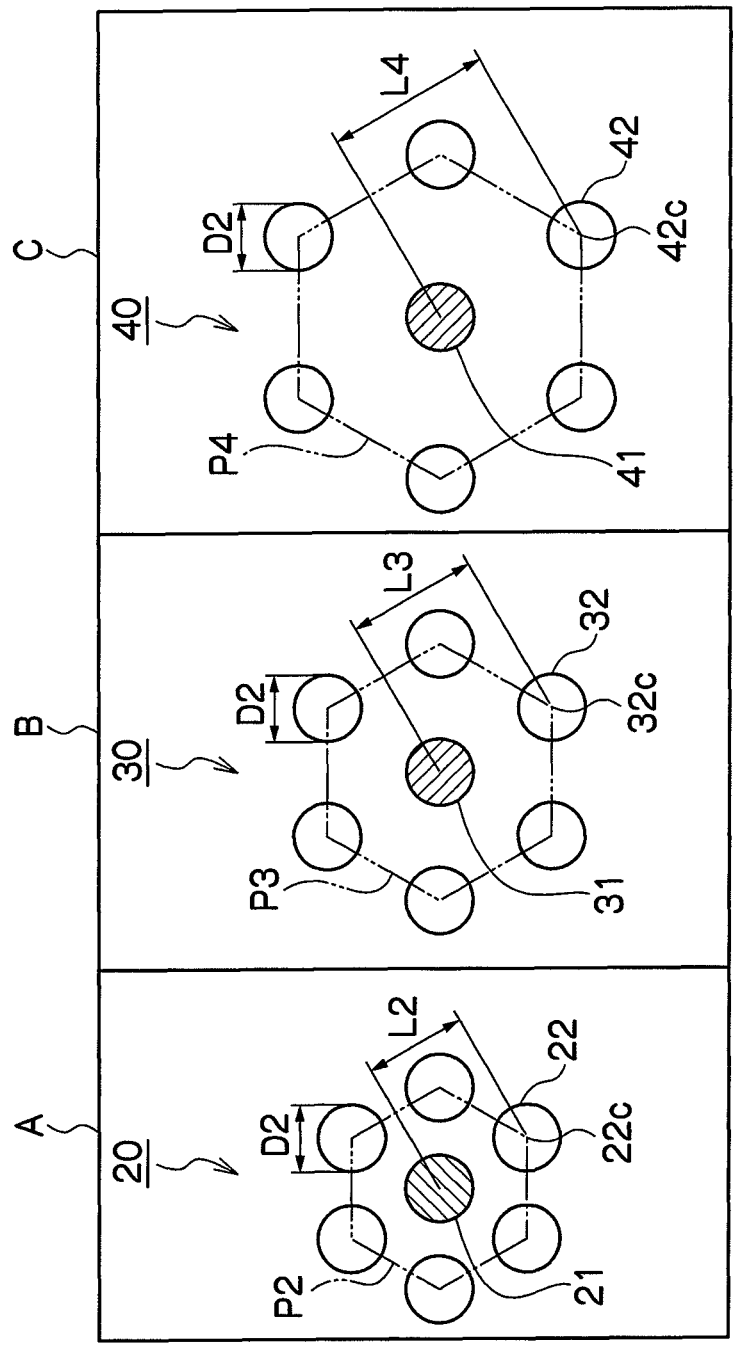
FIG. 4 is an explanatory view showing an example of a plurality of region sets, which are different from one another in the centroid distance and are used for a method for forming a tissue construct according to this embodiment.

FIG. 4 is an explanatory view showing an example of a plurality of region sets which are different from one another in the centroid distance. A first region set 20 shown in FIG. 4A has one specific region 21 and six adjacent regions 22 which are formed as circular regions with a fixed diameter D2 equal to one another. The center distance L2 between the specific region 21 and the respective adjacent regions 22 is equal to one another. Further, a second region set 30 shown in FIG. 4B has one specific region 31 and six adjacent regions 32 which are formed as circular regions with a diameter D2 which is the same as that of the specific region 21 and the respective adjacent regions 22 included in the first region set 20, and the center distance L3 between the specific region 31 and the respective adjacent regions 32 is larger than the center distance L2 in the first region set 20. Further, a third region set 40 shown in FIG. 4C has one specific region 41 and six adjacent regions 42 which are formed as circular regions with a diameter D2 which is the same as that of the specific region 21 and the respective adjacent regions 22 included in the first region set 20, and the center distance L4 between the specific region 41 and the respective adjacent regions 42 is larger than the center distance L3 in the second region set 30.

In the preparation step, for example, as shown in FIG. 4, a plurality of porous film surfaces having any one region set different from one another selected from the first region set 20, the second region set 30 and the third region set 40, each of which has the specific region 21, 31 or 41, and the adjacent regions 22, 32 or 42 with a diameter D2 equal to one another and in which the regular hexagons P2, P3 and P4 formed by connecting the center points of 22c, 32c and 42c of the adjacent regions 22, 32 and 42, respectively, are similar to one another, formed thereon are prepared. That is, in this preparation step, for example, the first porous film surface on which at least one first region set 20 is formed, the second porous film surface on which at least one second region set 30 is formed, and the third porous film surface on which at least one third region set 40 is formed are prepared. In this case, the first porous film surface, the second porous film surface and the third porous film surface may be prepared as the respective surfaces of three porous films formed separately from one another, or may be prepared as three different portions on one surface of one porous film. That is, the porous film of the present invention may have a plurality of region sets, each of the region sets including one cell adhesive region and other cell adhesive regions adjacent thereto and separated by the cell non-adhesive region and the respective region sets having a different centroid distance.

Figure 5:
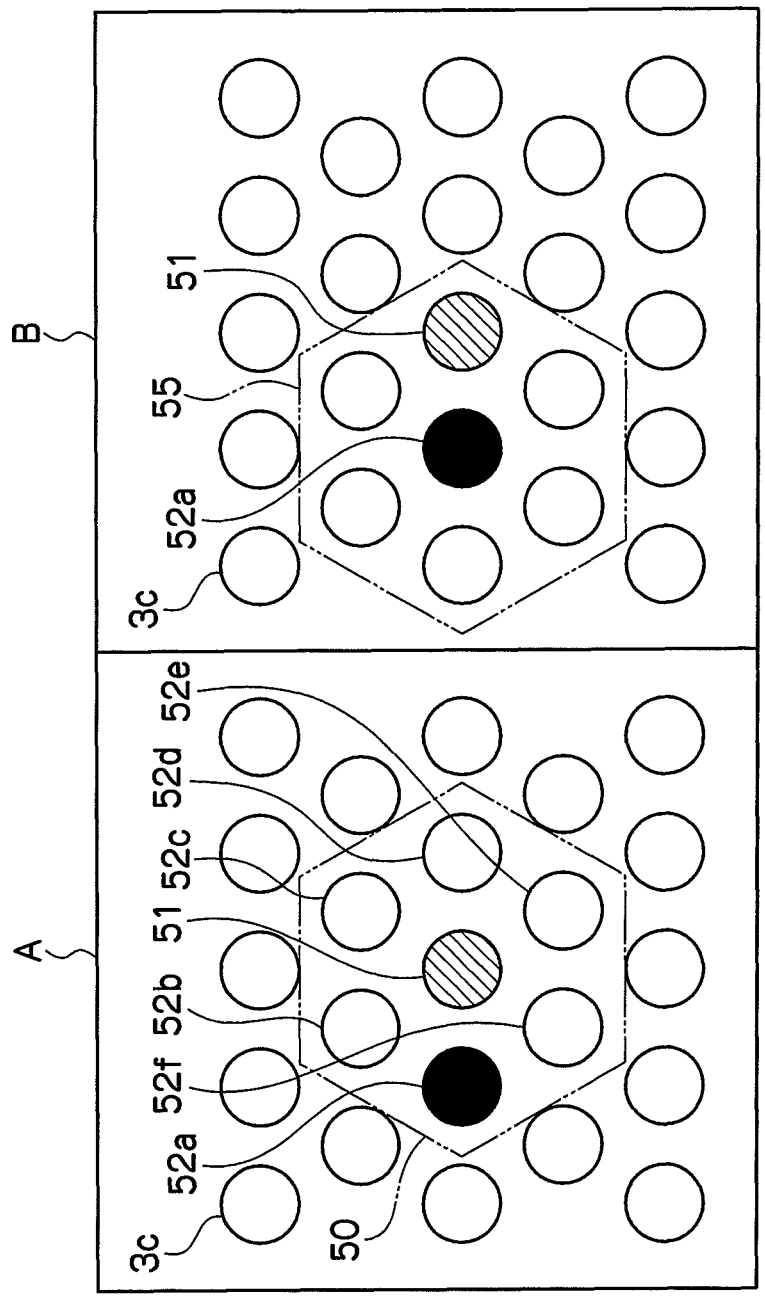
FIG. 5 is an explanatory view showing an example of a porous film surface having a region set formed thereon, which is used in a method for forming a tissue construct according to this embodiment.

The region set is conveniently specified by focusing attention on one of the plurality of surface regions as a specific region. Therefore, the specific region of a certain region set is one of the plurality of adjacent regions of another region set in some cases. FIG. 5 is an explanatory view showing a portion including a plurality of region sets among a plurality of surface regions 3c formed on a porous film surface 2. In a region set 50 shown in FIG. 5A, attention is paid on one surface region 51 indicated by the hatched circle as a specific region among a plurality of surface regions 3c. Also, when attention is paid on one surface region 52a indicated by the solid circle among the six surface regions 52a, 52b, 52c, 52d, 52e and 52f adjacent to the surface region 51, another region set 55 including the specific region 51 of the region set shown in FIG. 5A as one of the six adjacent regions is specified.

Figure 6:
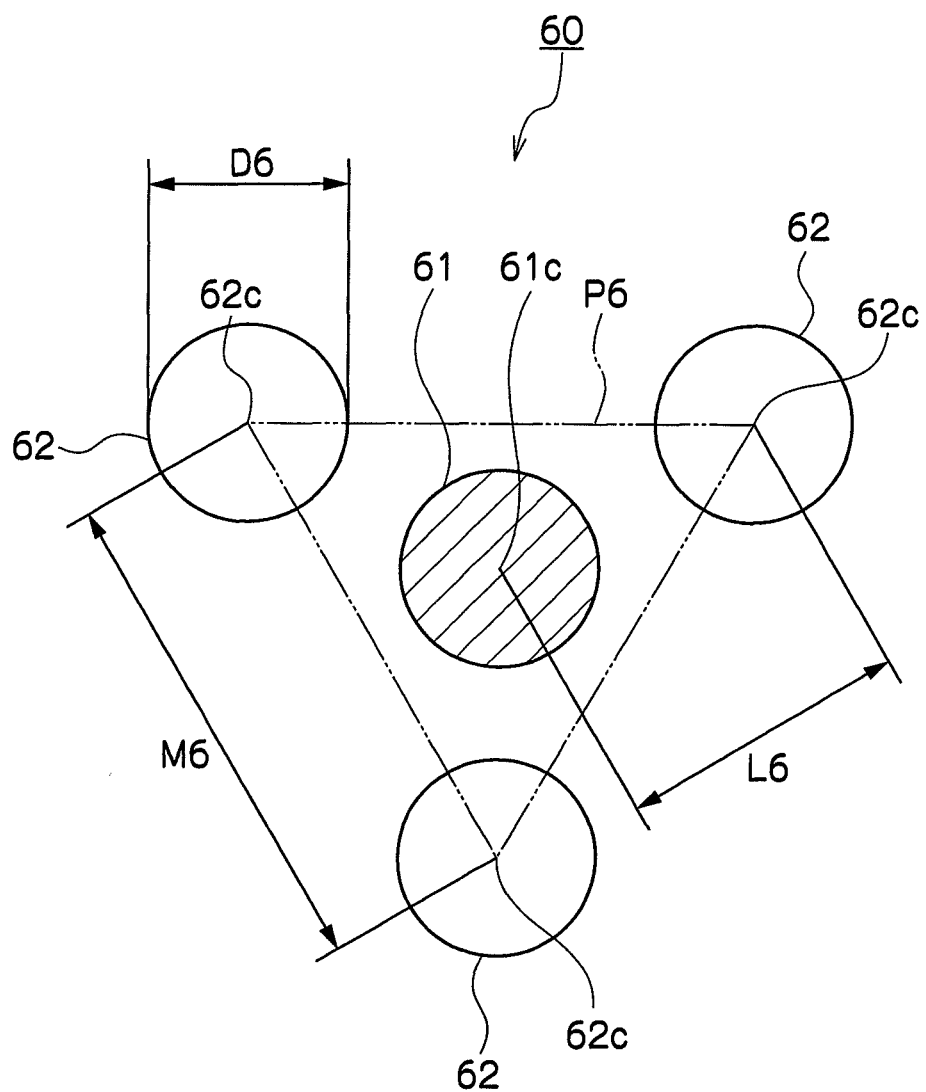
FIG. 6 is an explanatory view showing another example of a region set, which is used in a method for forming a tissue construct according to this embodiment.

Further, the number of adjacent regions included in a region set and a positional relationship between a specific region and adjacent regions are not limited to those shown in FIGS. 1 to 5. FIG. 6 is an explanatory view showing another example of region set. A region set 60 shown in FIG. 6 has one specific region 61 (a region indicated by the hatched circle in FIG. 6) and three adjacent regions 62 located around the specific region 61, which are formed in the form of a circle with a diameter D6 equal to one another, and the center distance L6 between the specific region 61 and the respective adjacent regions 62 is equal to one another. Further, the specific region 61 is located in a regular triangle P6 formed by connecting the respective center points 62c of the three adjacent regions 62 such that its center point 61c coincides with the centroid point of the regular triangle P6. Further, in this region set 60, the length M6 of the respective three sides of the regular triangle P6 is larger than the center distance L6.

Figure 7:
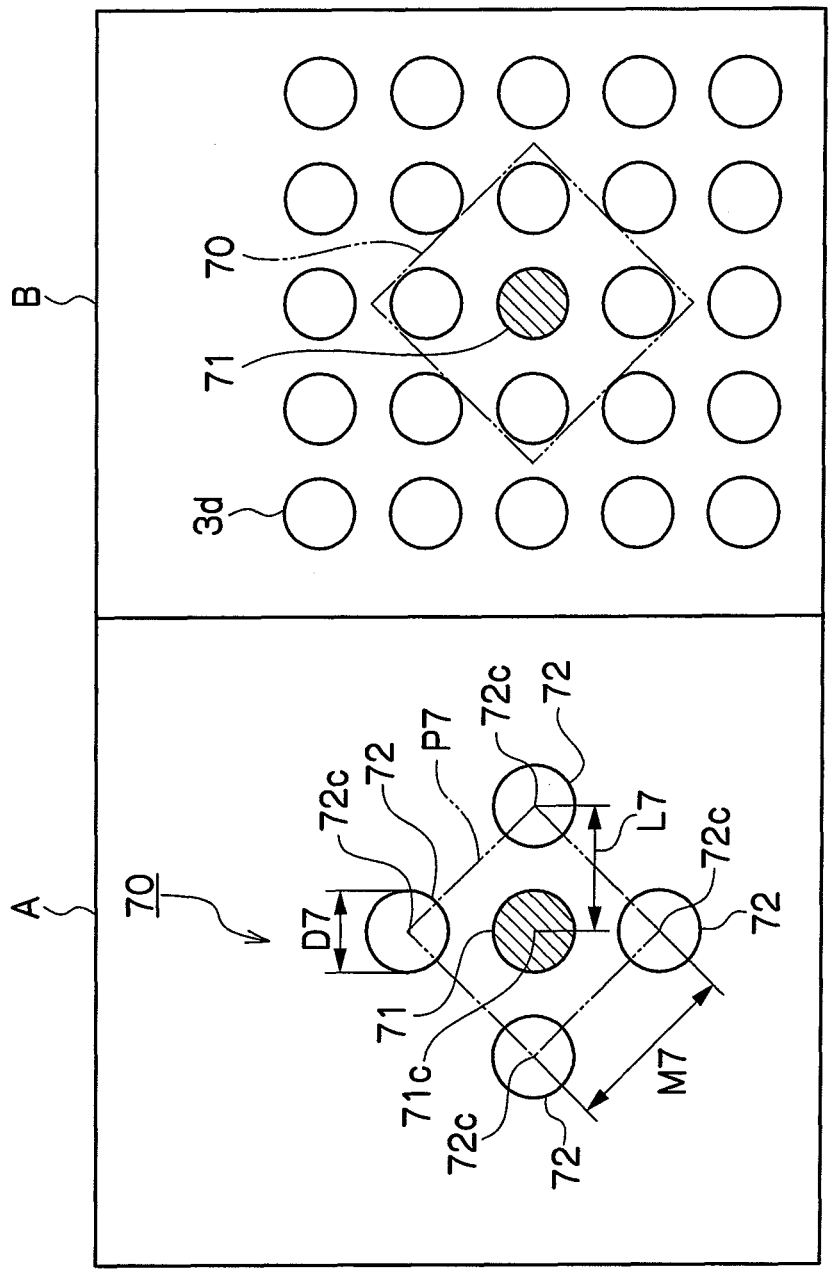
FIG. 7 is an explanatory view showing still another example of a region set, which is used in a method for forming a tissue construct according to this embodiment.

FIG. 7 is an explanatory view showing still another example of region set. A region set 70 shown in FIG. 7A has one specific region 71 (a region indicated by the hatched circle in FIGS. 7A and 7B) and four adjacent regions 72 located around the specific region 71, which are formed in the form of a circle with a diameter D7 equal to one another, and the center distance L7 between the specific region 71 and the respective adjacent regions 72 is equal to one another. The specific region 71 is located in a square P7 formed by connecting the respective center points 72c of the four adjacent regions 72 such that its center point 71c coincides with the centroid point of the square P7. Further, in this region set 70, the length M7 of the respective four sides of the square P7 is larger than the center distance L7. In this case, in the preparation step, for example, as shown in FIG. 7B, a porous film surface on which a plurality of surface regions 3d regularly arranged vertically and horizontally at a predetermined center distance L7 are formed such that the region set 70 shown in FIG. 7A is included in a portion thereof.

The form of the respective surface regions is not limited to a circular form as described above, and for example, it may be in the form of an oval or a polygon. A polygon formed by connecting the centroid points of adjacent regions is not limited to a regular polygon, and may be, for example, other polygon. A porous film on which respective surface regions are formed is not limited to a flat plate, and may be, for example, a film or a membrane with high flexibility or the like. Further, a cell adhesive surface region surrounded by a cell non-adhesive peripheral surface may be formed as a portion of a bottom surface of a cavity as shown in FIG. 2. That is, for example, it is also possible to form a cell adhesive surface region in the center which is a portion of the circular bottom surface of a cavity and further to form a portion or the whole of the remaining area of the circular bottom surface surrounding the cell adhesive surface region as a cell non-adhesive peripheral surface.

In this way, by forming cell adhesive regions 3a on the surface 2 of the porous film 1, the tissue construct-forming substrate of the invention can be obtained.

This tissue construct-forming substrate is useful for forming a three-dimensional tissue construct in cell culture.

Next, the culture step using the tissue construct-forming substrate of the invention is described.

In this culture step, proliferating cells are cultured in a plurality of cell adhesive regions 3a included in each region set 10 on the porous film surface 2. As the cells to be cultured, any cells can be used regardless of the species of derived animal, types of organs or tissues, or the like, or whether the cells are proliferative or nonproliferative as long as they can three-dimensionally aggregate to one another to form a three-dimensional tissue construct under a predetermined condition. As specific examples thereof, proliferable cells from primary cells collected from the liver, pancreas, kidney, nerve, skin or the like derived from humans, or non-human animals (for example, monkeys, pigs, dogs, rats, mice, or the like), undifferentiated stem cells, ES cells derived from embryos (embryonic stem cells) and established cell lines, cells obtained by subjecting these cells to genetic manipulation and the like can be preferably used. Further, one kind of cell can be used alone, and also two or more kinds of cells can be used by allowing them to coexist at a given ratio.

As a culture medium to be used when cells are cultured, a culture medium with any composition can be used as long as it is an aqueous solution containing necessary salts, nutritional components and the like at appropriate concentrations so as to maintain the viability status and function of the cells and the like. Specifically, for example, as this culture medium, a culture medium obtained by adding a growth factor, an antibiotic or the like to a minimal essential medium such as Dulbecco's Modified Eagle's medium (DMEM), a so-called physiological saline or the like can be preferably used.

In this culture step, cells maintained in a specific region and each adjacent region which are formed as the cell adhesive regions 3a shown in FIG. 1 by adhering thereto, and cells maintained in a specific region and each adjacent region which are formed as the cell adhesive regions 3a shown in FIG. 2 by adhering thereto gradually overlap with one another in the specific region and each adjacent region with the lapse of culture time and three-dimensionally aggregate to form a three-dimensional tissue construct. That is, cells adhering to a specific region according to the cell adhesive surface region 3a and each adjacent region first two-dimensionally proliferate in the specific region and each adjacent region, and thereafter, three-dimensionally proliferate such that they are stacked with one another thereby to form a tissue construct with a predetermined thickness.

The size of this tissue construct formed in the specific region and each adjacent region can increase with the lapse of culture time by proliferating the cells contained in the tissue construct. However, in the present method, the size of the tissue construct formed at least in the specific region is maintained to be a fixed size according to the centroid distance between the specific region and each adjacent region. That is, for example, in the culture step, the size of the tissue construct formed in the specific region gradually increases during a predetermined period of time after initiation of culture, and, after the size reached a predetermined size defined by the centroid distance between the specific region and each adjacent region, its increase is prevented, and the size is maintained to be a predetermined size throughout the culture period thereafter.

Accordingly, for example, in the case where a first porous film surface having a region set in which the centroid distance is a first value formed thereon and a second porous film surface having a region set in which the centroid distance is predetermined times larger than the first value formed thereon are prepared in the preparation step, in the specific region of the second porous film surface, a tissue construct with a size which is predetermined times larger than that of a tissue construct formed in the specific region of the first porous film surface can be formed in the culture step. Specifically, for example, in the case where a first porous film surface having a first region set 20 shown in FIG. 4A formed thereon and a second porous film surface having a second region set 30 shown in FIG. 4B formed thereon are prepared in the preparation step, in the culture step, a ratio of the size of a tissue construct formed in the second specific region 31 included in the second region set 30 to the size of a tissue construct formed in the first specific region 21 included in the first region set 20 is almost equal to a ratio of the centroid distance L3 of the second region set 30 to the centroid distance L2 of the first region set 20.

The size of a tissue construct is, for example, a representative length of the form when the outer shape of the tissue construct is projected on the porous film surface or a thickness of the tissue construct on the porous film surface. That is, for example, in the case where a tissue construct is in a substantially spherical shape (including the case where a tissue construct adheres to the cell adhesive surface region 3a and is in a dome shape or a substantially spherical shape, and the case where a tissue construct is suspended in a culture medium in the cell non-adhesive surface region 4a and is in a substantially spherical shape are included), the size of the tissue construct may be the diameter of the circular form obtained by projecting the outer shape of the tissue construct onto the porous film surface. Such a tissue construct in a substantially spherical shape may be formed regardless of the shape of the cell adhesive surface region 3a, and it can be preferably formed in a circular or polygonal surface region 3a, and particularly preferably formed in a circular surface region 3a. Further, in the case where the shape obtained by projecting the outer shape of a tissue construct onto the porous film surface is, for example, oval, the size of the tissue construct is the long axis or the short axis of the oval body. Further, in the case where a tissue construct, for example, extends in a string shape along with the porous film surface, the size of the string-shaped tissue construct may be the length in the long axis direction. Further, in the case where a tissue construct is, for example, in a dome shape such as a semispherical shape, the size of the tissue construct may be the diameter of the circular form obtained by projecting the outer shape of the tissue construct onto the porous film surface, or the thickness of the dome raised from the porous film surface.

Further, the present method may include a step in which calibration data showing a correlation between the centroid distance of the porous film surface to be prepared in the preparation step and the size of a tissue construct to be formed in the culture step is acquired (hereinafter referred to as a "data acquisition step"). In this data acquisition step, first, the size of a tissue construct formed in the culture step is measured. That is, for example, by using a phase contrast microscope, a fluorescence microscope, an electron microscope or the like, an image obtained by photographing a tissue construct formed on a porous film surface is obtained, and the image is analyzed using a computer installed with a predetermined image analysis software, and thus, the size of the tissue construct is quantitatively measured.

Then, in this data acquisition step, calibration data in which the size of a tissue construct measured is linked with the centroid distance between the specific region and each adjacent region having the tissue construct formed therein was constructed. That is, for example, a spherical tissue construct with a first diameter is formed in a first specific region 21 shown in FIG. 4A, and also a spherical tissue construct with a second diameter is formed in a second specific region 31 shown in FIG. 4B. Then, the first diameter is linked with the first centroid distance L2 related to the first specific region 21, and also the second diameter is linked with the second centroid distance L3 related to the second specific region 31.

This calibration data is, for example, data that defines the centroid distance to be set for forming a tissue construct with a predetermined size. That is, this calibration data is a data table or function in which the size of a tissue construct and the centroid distance for forming a tissue construct with the predetermined size are linked with each other.

The present method may include a step in which a centroid distance for forming a tissue construct with a desired size is determined based on the calibration data acquired in the calibration data acquisition step (hereinafter referred to as a "determination step"). In this determination step, for example, from a correlation between the size of a tissue construct and the centroid distance defined by the calibration data which has already been acquired, a centroid distance which has been linked with a desired size is determined. That is, in the calibration data, for example, a first centroid distance related to a specific region 21 shown in FIG. 4A is determined to be the first centroid distance L2. In this case, in the preparation step, a porous film surface is prepared on which a plurality of region sets are formed, with each region set including a specified region of which the centroid distance with each adjacent region is the first centroid distance L2 determined in the determination step. Then, in the culture step, by culturing proliferating cells in the specified regions and adjacent regions, respectively, a plurality of constructs having a size controlled at the first size can be formed in each of the specified regions.

Further, when calibration data that defines a proportional relationship between the size of a tissue construct and a centroid distance has been acquired, for example, the centroid distance corresponding to a desired size can be determined in the determination step based on the relational expression defining the proportional relationship. Further, when the centroid distance for forming a tissue construct with a desired size cannot be determined based on the calibration data already acquired, as described above, for example, the centroid distance for forming a tissue construct with the desired size is screened by forming a tissue construct in each specified region in a plurality of region sets having different centroid distances from one another. Then, in the determination step, the centroid distance of the region set in which a tissue construct with the desired size was formed is determined to be the centroid distance corresponding to the desired size based on the calibration data acquired in the data acquisition step in the screening.

In the present method, the respective steps may be carried out on a plurality of porous film surfaces which are different from one another in the centroid distance all at a time. Alternatively, the respective steps may be carried out on a porous film surface among a plurality of porous film surfaces which are different from one another in the centroid distance and this procedure may be repeated with respect to each centroid distance. That is, for example, a first cycle, in which a first porous film surface having a first centroid distance is prepared and then, a tissue construct is formed on the first porous film surface, is carried out. Then, a second cycle, in which a second porous film surface having a second centroid distance different from the first centroid distance is prepared and then, a tissue construct is formed on the second porous film surface, may further be carried out.

Further, a tissue construct-forming kit (hereinafter referred to as a "present kit") according to this embodiment includes a first porous film on which a specific region and a plurality of adjacent regions are formed such that the centroid distance becomes a first distance, and a second porous film on which a specific region and a plurality of adjacent regions are formed such that the centroid distance becomes a second distance different from the first distance. That is, the present kit includes a plurality of porous film surfaces on which any one of the region sets having a centroid distance different from one another among the plurality of region sets which are different from one another in the centroid distance is formed. Specifically, for example, the present kit includes a first porous film surface on which a first region set 20 shown in FIG. 4A is formed, a second porous film surface on which a second region set 30 shown in FIG. 4B is formed, and a third porous film surface on which a third region set 40 shown in FIG. 4C is formed.

The present kit may include a plurality of porous films which are different from one another in the centroid distance of the region set as different portions on one porous film. That is, each of a plurality of porous film surfaces which are different from one another in the centroid distance of the region set included in the present kit may be a portion which is different from one another on one porous film surface. Specifically, for example, the present kit may include a plurality of porous films, in which a plurality of region sets are formed on surface portions different from one another as follows: At least one first region set 20 shown in FIG. 4A is formed in one portion on a porous film surface included in the present kit, at least one second region set 30 shown in FIG. 4B is formed in another portion on the surface, and at least one third region set 40 shown in FIG. 4C is formed on still another portion on the surface.

Further, each of a plurality of porous film surfaces which are different from one another in the centroid distance of the region set formed thereon included in the present kit may be each surface of a plurality of porous films formed separately from one another. That is, in this case, for example, the present kit includes a first porous film having a surface on which at least one first region set 20 shown in FIG. 4A is formed, a second porous film formed separately from the first porous film and having a surface on which at least one second region set 30 shown in FIG. 4B is formed, and a third porous film formed separately from the first porous film and the second porous film and having a surface on which at least one third region set 40 shown in FIG. 4C is formed.

Then, by culturing proliferating cells in the specific region and respective adjacent regions formed on each of the plurality of porous film surfaces included in the present kit, a tissue construct with a size defined by the centroid distance of each region set can be formed in the specific region on each porous film surface. That is, as described above, for example, in the case where the present kit includes a plurality of porous film surfaces such that the centroid distance is regularly changed among the plurality of porous film surfaces, the size of a tissue construct to be formed in each of the specific regions on the plurality of porous film surfaces is regularly changed according to the centroid distance among the plurality of porous film surfaces. Specifically, for example, in the case where the present kit includes a first porous film surface on which a first region set 20 shown in FIG. 4A is formed, a second porous film surface on which a second region set 30 shown in FIG. 4B is formed, and a third porous film surface on which a third region set 40 shown in FIG. 4C is formed, and the center distance L2 of the first region set 20, the center distance L3 of the second region set 30, and the center distance L4 of the third region set 40 are increased in sequence at a fixed rate, a first tissue construct formed in the first region set 20, a second tissue construct formed in the second region set 30, and a third tissue construct formed in the third region set 40 also can be increased in the size in sequence at the fixed rate.

Thus, with the use of the present kit, for example, a tissue construct array chip in which constructs with a size controlled according to the centroid distance are arranged regularly and at a high density on each porous film surface can be obtained. Further, by using such a tissue construct array chip, for example, a correlation between the responsiveness (sensitivity, toxicity or the like) of cells to drugs and the size of a tissue construct formed with the cells can be studied simply and accurately over a long period of time. Specifically, for example, by forming a plurality of constructs comprising cells derived from cancer with a size changed at a fixed rate according to the centroid distance on the porous film of the present kit, and measuring the responsiveness (change in the growth rate, survival rate or morphology of the cells contained in each tissue construct, or the like) of the constructs in a culture solution containing an anticancer agent, the correlation between the size of a tumor block in the living body and the drug efficacy of the anticancer agent can be appropriately predicted and evaluated.

Speaking of another embodiment of applying the tissue construct-forming kit of the invention, for example, according to the present kit, a centroid distance for forming a tissue construct with a desired size can be screened simply and accurately. Further, a tissue construct can be maintained in such a state that it is adhered to a cell-adhesive surface region of a porous film in the present kit. Further, a porous film included in the present kit is collected and can be used as a sheet sample. A porous film has relatively low cell adhesiveness compared with a related cell chip, therefore, it is also possible to collect and handle a tissue construct formed in each surface region with ease by suspending the tissue construct in a solution.

Further, the inventors found for the first time that by using a porous film as a substrate, a spheroid may be formed not only on the porous film surface on the side inoculated with cells, but also on the porous film surface opposite to the side inoculated with cells through the investigations involved in the invention. That is, it was found that as shown in schematic views of FIGS. 14A and 14B, by controlling the relationship between the hole size of the porous film and the size of cells to be cultured, spheroid formation can be selectively promoted not only on one side of the porous film surface, but on both sides, that is, also on the side opposite to the inoculated surface. Accordingly, the tissue construct-forming kit of the invention can also be applied to studies related to anisotropy of culture environments, development of coculture systems and the like, and its application range is wide.

EXAMPLES

Hereinafter, Examples of the present invention will be described, however, the invention is by no means limited to the following Examples.

Example 1

Preparation of Porous Film

Poly ε-caprolactone) (PCL, manufactured by Wako, weight average molecular weight: 70,000 to 100,000) and an amphiphilic polyacrylamide polymer (with the following structure, weight average molecular weight: 49,000) were mixed at a weight ratio of 10:1 and the mixture was dissolved in methylene chloride to give a final concentration of 0.5 mg/mL. This solution was casted on a glass dish (φ 90), and methylene chloride was evaporated under an atmosphere of a relative humidity of 80%, whereby a through-type honeycomb porous film A in which through-holes passing through the front and back surfaces of the film with a hole size of from 7 μm to 15 μm were arranged in a honeycomb pattern was obtained.

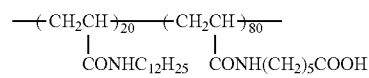

The structure of the obtained through-type honeycomb porous film A was observed using a field emission scanning electron microscope (S4300, manufactured by Hitachi High-Technologies Corporation), and the honeycomb structure in which holes with an average hole size of 11 μm were regularly arranged in a hexagonal pattern from a planar view could be confirmed. The distance between the centers of adjacent holes was almost about 16 μm. The holes formed a monolayer from the front surface to the back surface of the film, and the respective holes were in a spherical shape, and had a structure in which adjacent holes communicated with one another. Further, both of the upper and bottom surfaces of the holes were open, and the holes had a structure in which holes passed through the front and back surfaces of the film. The holes were distributed almost all over the surface except for a peripheral portion of casted area.

Preparation of Porous Film of Comparative Example 1

As a comparative sample, the following film was prepared. A flat plate mold (with a size of 20 mm×20 mm) in which cylindrical columns with a diameter of 10 μm and a height of 15 μm were regularly arranged in a hexagonal pattern such that the center distance of adjacent cylindrical columns was 15 μm was produced. Then, while keeping the temperature of the above-mentioned flat film at 40° C., the flat plate mold was pressed against the flat film at a load of 0.1 Pa for 30 seconds. Then, the film was released from the mold, whereby a non-through-type honeycomb film B in which cavities with a bottom (non-through holes) having a diameter of about 10 μm and a depth of about 15 μm were arranged in a hexagonal pattern on the surface such that the center distance between the cavities was about 15 μm was obtained.

Preparation of Tissue Construct-Forming Kit

A flat plate (24 mm×24 mm, thickness: 400 μm) made of polymethyl methacrylate (PMMA) was used as a supporting member 5b, and a tissue construct-forming kit A as shown in FIG. 2 was produced. That is, a pre-kit A composed of a porous film having a plurality of hexagon sets in which the bottom surface of the cavity 100 includes a cell adhesive region 3a and a cell non-adhesive region 4b formed thereon was produced.

Specifically, by subjecting a portion of the surface of this polymethyl methacrylate flat plate to perforation processing using a machining center (desktop NC microfabrication machine, manufactured by PMT Inc.) throughout the range of a 10 by 10 centimeters square, through-holes were produced therein by regularly arranging circular holes with a diameter of 300 μm such that the center distance between adjacent holes was 400 μm (a supporting member A).

Subsequently, the above-mentioned through-type honeycomb porous film A and the supporting member A were thermally compressed and fixed to each other, whereby a pre-kit A was obtained.

Subsequently, on the entire surface (on the side of the supporting member A) of this pre-kit A having the through-type honeycomb porous film fixed thereon, a platinum (Pt) thin film with a thickness of 9 nm was formed using a sputtering device (E-1030, Hitachi, Ltd.). At the same time, a stamp made of poly(dimethyl siloxane) (PDMS) having a plurality of cylindrical protrusions with a diameter of 100 μm and a length of 200 μm was produced by molding. That is, the stamp was produced such that the center distance between the cylindrical sections having a diameter at the top of 100 μm became 400 μm in response to the position of the respective surface regions of the hexagon set in the range of a 10 by 10 mm square.

Then, cell adhesive regions 3a were formed on the porous film surface by a microcontact printing method using the above-mentioned stamp. That is, a collagen solution containing 1.5 mg/mL of collagen (Cellmatrix, Nitta Gelatin Co.) prepared as a cell adhesive substance to be fixed in each surface region was prepared, and the top of the cylindrical protrusions of the stamp was dipped in the collagen solution, whereby the collagen solution was applied to the circular top surface of the cylindrical protrusions of the stamp. Then, the top of the cylindrical protrusions of the stamp was pressed against the porous film surface vapor-deposited with platinum, whereby the collagen solution applied to the top of the cylindrical protrusions was applied to the porous film surface. Further, the collagen solution applied to this porous film surface was dried under a nitrogen atmosphere, whereby cell adhesive regions 3a in which collagen was fixed was formed at a position corresponding to the top of the cylindrical protrusions of the stamp. That is, collagen with a diameter of 100 μm was placed in the center of each microcavity with a diameter of 300 μm.

Further, in the portion 4b other than the surface region within the porous film surface, a cell non-adhesive substance was fixed as follows. That is, as the cell non-adhesive substance to be fixed on the surface surrounding each surface region, a synthetic polymer (having the following structure: NOF Corporation) having a polyethylene glycol (PEG) chain with a weight average molecular weight of 30,000 and a thiol group was prepared.

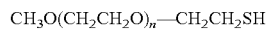

Then, the porous film surface on which the surface regions were formed as described above was soaked in an ethanol solution containing this cell non-adhesive substance at a concentration of 5 mM, and a specific chemical bond is formed between the thiol group of the cell non-adhesive substance and an exposed moiety in the platinum thin film formed on the porous film surface (that is, a moiety other than the surface regions on the porous film surface) under a nitrogen atmosphere, whereby the cell non-adhesive substance was fixed on the platinum thin film surface. Thereafter, under a nitrogen atmosphere, the porous film surface on which this cell non-adhesive substance was fixed was sufficiently dried, and then the porous film surface was soaked in 70% ethanol, whereby an excess cell non-adhesive substance was removed from the porous film surface and also the porous film surface was sterilized.

Subsequently, preparation and culture of primary rat hepatocytes were carried out as follows.

First, in order to prepare primary rat hepatocytes, 150 mL of a 0.5 mg/mL collagenase (manufactured by Wako Pure Chemical Industries, Ltd.) solution was prepared. After a cannula was introduced into the portal vein (the blood vessel which leads to the liver) of a male Wistar-line rat at 7 weeks of age (weight: 250 g) and the blood was drawn for 5 minutes at 30 mL/min, the collagenase solution heated to 37° C. was fed thereinto for 10 minutes at 15 ml/min. The liver treated with collagenase was put into a culture solution and the hepatocytes were dispersed using a scalpel and a pipette. The resulting hepatocyte suspension was washed three times thereby to remove cells other than hepatocytes (at a purity of 95% or higher). The thus isolated hepatocytes were used as seed cells for a culture experiment mentioned below.

For culture of hepatocytes, a serum-free medium obtained by adding 60 mg/L of proline, 50 mg/ml of an epidermal growth factor (EGF, manufactured by Funakoshi), 10 mg/L of insulin (manufactured by SIGMA), 7.5 mg/L of hydrocortisone (manufactured by Wako Pure Chemical Industries, Ltd.), 0.1 μM of copper sulfate pentahydrate (manufactured by Wako Pure Chemical Industries, Ltd.), 3 μg/L of selenic acid (manufactured by Wako Pure Chemical Industries, Ltd.), 50 pM of zinc sulfate heptahydrate (manufactured by Wako Pure Chemical Industries, Ltd.), 50 μg/L of linoleic acid (manufactured by SIGMA), 58.8 mg/L of penicillin (manufactured by Meiji Seika), 100 mg/L of streptomycin (manufactured by Meiji Seika), 1.05 g/L of sodium hydrogen carbonate (manufactured by Wako Pure Chemical. Industries, Ltd.), and 1.19 g/L of 2-[4-(2-hydroxyethyl)-1-piperazinyl] ethanesulfonic acid (HEPES, manufactured by Dojindo) to 13.5 g/L of Dulbecco's Modified Eagle's medium was used. In this experimental system, rat hepatocytes do not proliferate.

After the above-mentioned tissue construct-forming kit A was subjected to a sterilization treatment, it was disposed at the bottom of a culture container (diameter: 35 mm, manufactured by Falcon) made of polystyrene, and then, rat hepatocytes were inoculated on the surface of the tissue construct-forming kit in the culture container at a cell density of $1.7 \times 10^5$. The culture was carried out in a 5% carbon dioxide and 95% air atmosphere, and medium replacement was carried out every two days using 2 mL of the above-mentioned fresh medium.

In order to evaluate the state of obtained cultured hepatocytes, the cell morphology was observed using a phase contrast microscope at each period of culture. Further, in a condition where a spheroid was formed, the particle size was measured, and the spheroidal particle size distribution was evaluated. Here, in the measurement of spheroidal particle size, an image analysis software WinROOF (manufactured by Mitani Corporation) was used, and the particle size of 100 spheroids were measured per one condition, and the particle size distribution was obtained. It was confirmed that cells in a dispersed state at the initial stage of culture were gradually assembled, and the cells were bound and aggregated and a spheroid which was a three-dimensional cell tissue construct was formed.

An albumin secretion activity, which is a function of hepatocytes, was evaluated by the following method on day 7 after initiation of culture. Albumin secreted in the culture medium was determined by an enzyme-labeled immunoassay, and the obtained value was converted into an albumin secretion rate per unit cell number (μg/$10^6$ cells/day). The measurement of cell number was carried out using the DNA-DAPI (4,6-diamidino-2-phenylindole, manufactured by Wako Pure Chemical Industries, Ltd.) fluorescence method. That is, a calibration curve between DNA extracted from a fixed number of cells and the fluorescence intensity of DNA-DAPI was constructed, and the number of cells cultured was calculated based on this relation. Based on the thus obtained cell number, an albumine secretion rate per the above-mentioned cell number ($10^6$ cells) was calculated.

Comparative Example 1

An experiment was carried out in a similar manner using the tissue construct-forming kit B produced by the same method except that the non-through-type flat film B obtained as described above was used in place of the through-type porous film A as a comparative sample.

Figure 8A:
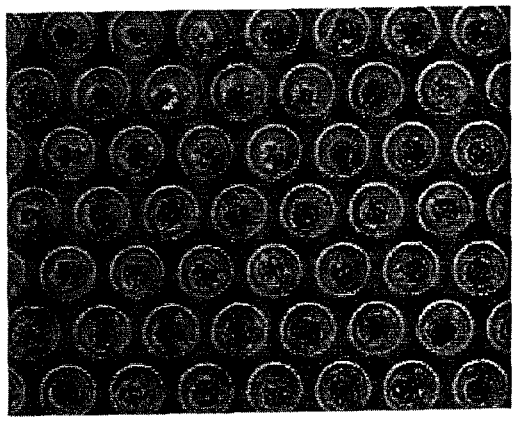
FIGS. 8A to 8E are light micrographs showing the morphology of spheroids formed in Examples 1 to 5.
Figure 10:
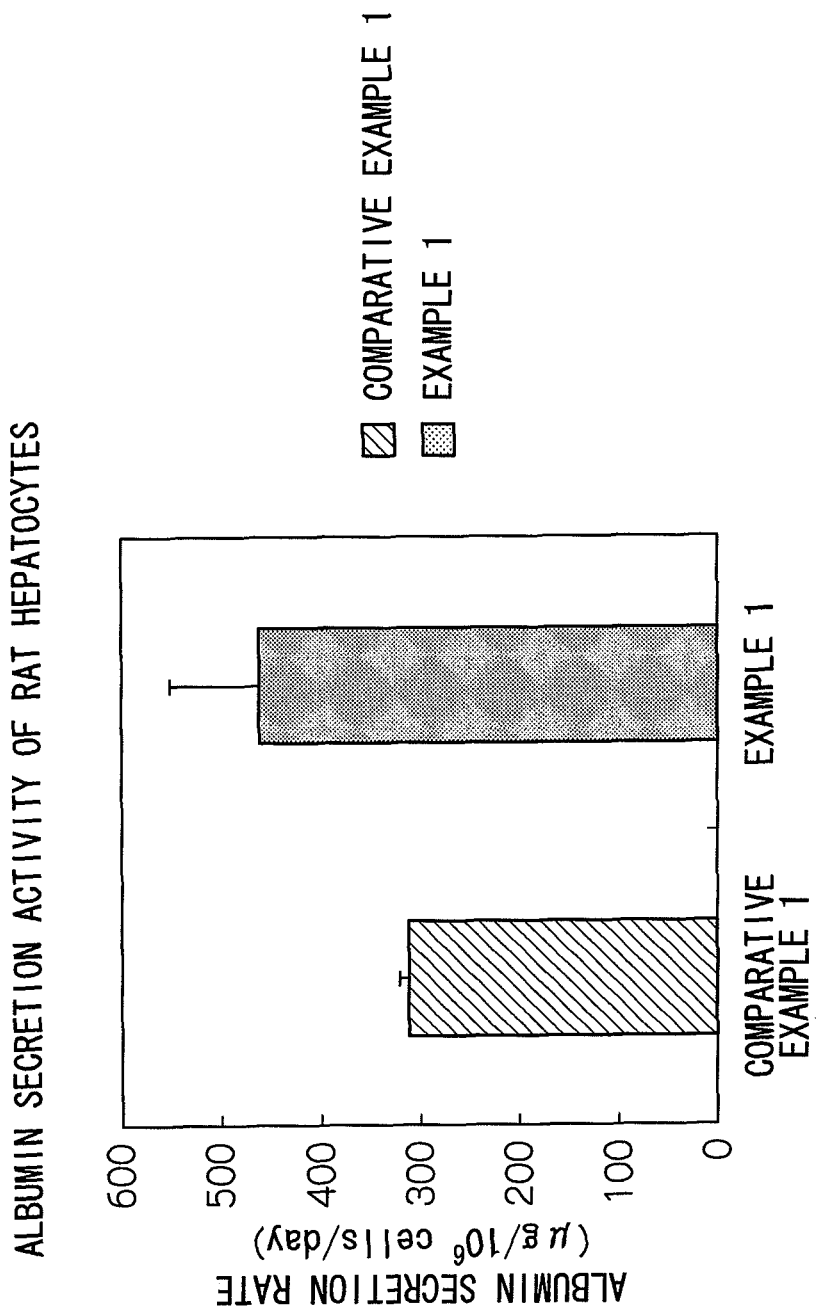
FIG. 10 is a graph showing the albumin secretion activity of constructs formed in Example 1 and Comparative example 1.

FIG. 8A shows the morphology of formed rat hepatocyte spheroids, FIG. 9 shows the change in the spheroidal particle size and FIG. 10 shows the results of albumin secretion activity of rat hepatocytes. The rat hepatocytes formed regularly arranged spheroids on the tissue construct-forming kit A (see FIG. 8A), and their particle size was kept constant (FIG. 9). Further, from FIG. 10, it was found that the albumin secretion activity of hepatocytes which were cultured to form a spheroid by the method for forming a tissue construct of the invention was higher compared with the case where a porous film was not used.

Example 2

As the proliferating cells, a HepG2 cell line (RCB1648, RIKEN Cell Bank), which is a cell line derived from human hepatoblastoma, was used. As the culture medium, a serum-containing culture medium obtained by adding 58.8 mg/L of penicillin (manufactured by Meiji Seika), 100 mg/L of streptomycin (manufactured by Meiji Seika), 2.2 g/L of sodium hydrogen carbonate (manufactured by Wako Pure Chemical Industries, Ltd.) and 10% of fetal bovine serum (FBS, manufactured by Invitrogen) to 10.8 g/L of Williams' medium E (manufactured by SIGMA) was prepared and used.

After the above-mentioned tissue construct-forming kit A was subjected to a sterilization treatment, it was disposed at the bottom of a culture container (diameter: 35 mm, manufactured by Falcon) made of polystyrene, and then, HepG2 cells were inoculated on the surface of the tissue construct-forming kit in the culture container at a cell density of 1.0× $10^5$. The culture was carried out in a 5% carbon dioxide and 95% air atmosphere, and medium replacement were carried out every two days using 2 mL of the above-mentioned fresh medium.

Culture and an evaluation experiment were carried out in the same manner as in Example 1 except for the above-mentioned point. Further, culture and an evaluation experiment for comparison were carried out in the same manner as in Comparative example 1 except for the above-mentioned point.

Figure 8B:
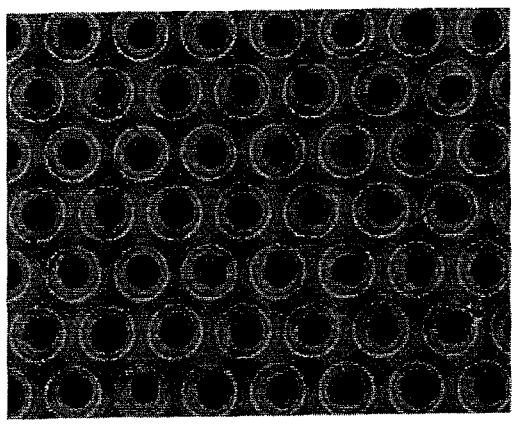
Figure 11:
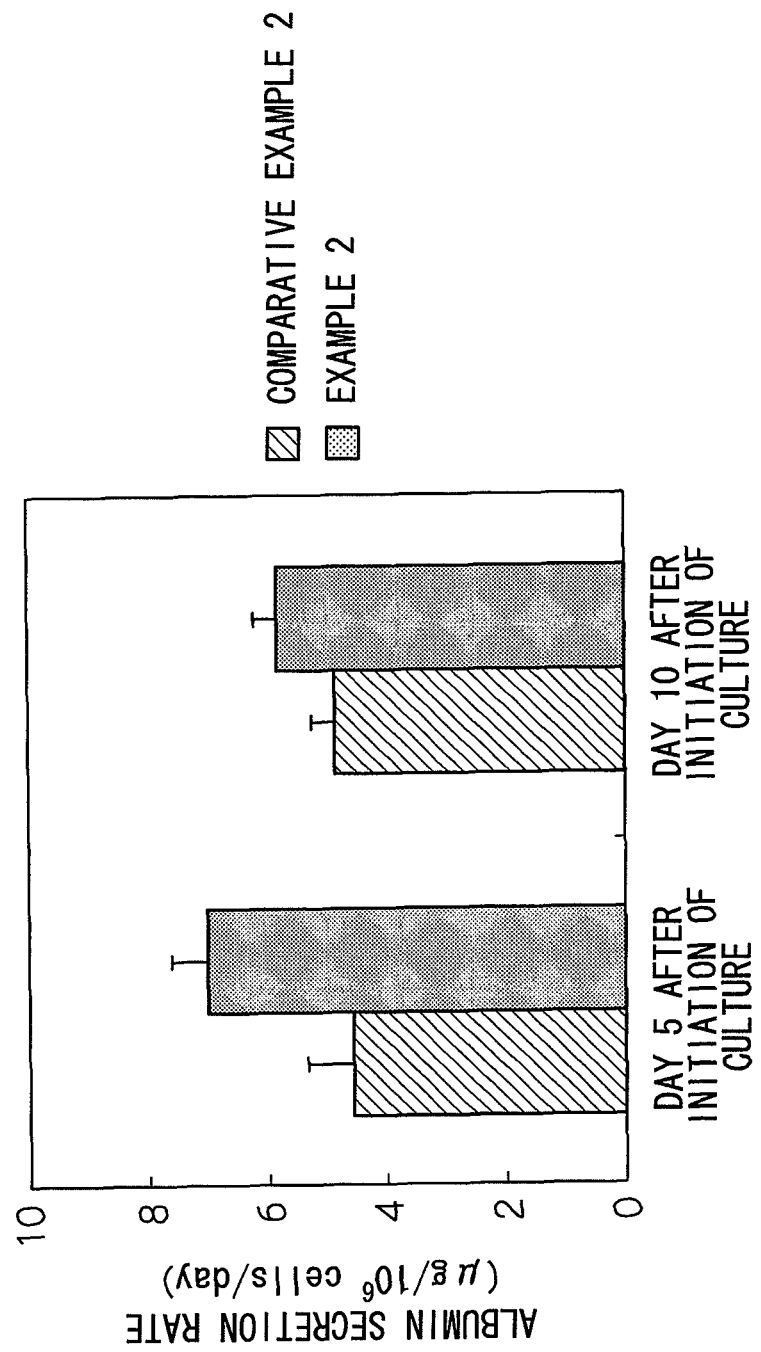
FIG. 11 is a graph showing the albumin secretion activity of constructs formed in Example 2 and Comparative example 2.

FIG. 8B shows the morphology of formed HepG2 cell spheroids, FIG. 9 shows the change in the spheroidal particle size and FIG. 11 shows the results of albumin secretion activity of HepG2 cells. The HepG2 cells formed regularly arranged spheroids on the tissue construct-forming kit A (see FIG. 8B). Further, the spheroidal particle size increased as the cells proliferated at the initial stage of culture, however, on day 10 after initiation of culture and thereafter, the particle size was kept constant (FIG. 9). Further, from FIG. 11, it was found that the albumin secretion activity of HepG2 cells which were cultured to form a spheroid by the method for forming a tissue construct of the invention was higher compared with the case where a porous film was not used.

Example 3

Culture and an evaluation experiment was carried out in the same manner as in Example 2 except that as the proliferating cells, a HuH7 cell line (RCB 1366, RIKEN Cell Bank), which is a cell line derived from human hepatoma, was used. Further, culture and an evaluation experiment for comparison were carried out in the same manner as in Comparative example 2 except for the above-mentioned point.

Figure 8C:
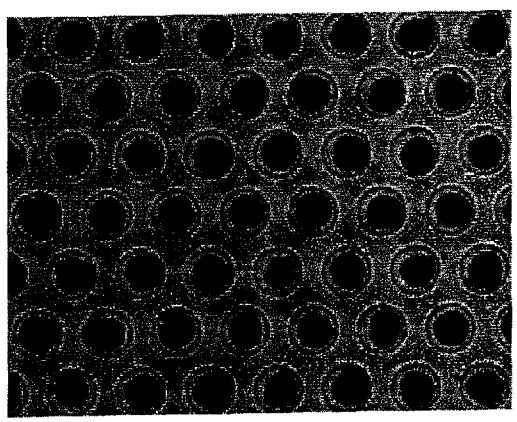
Figure 12:
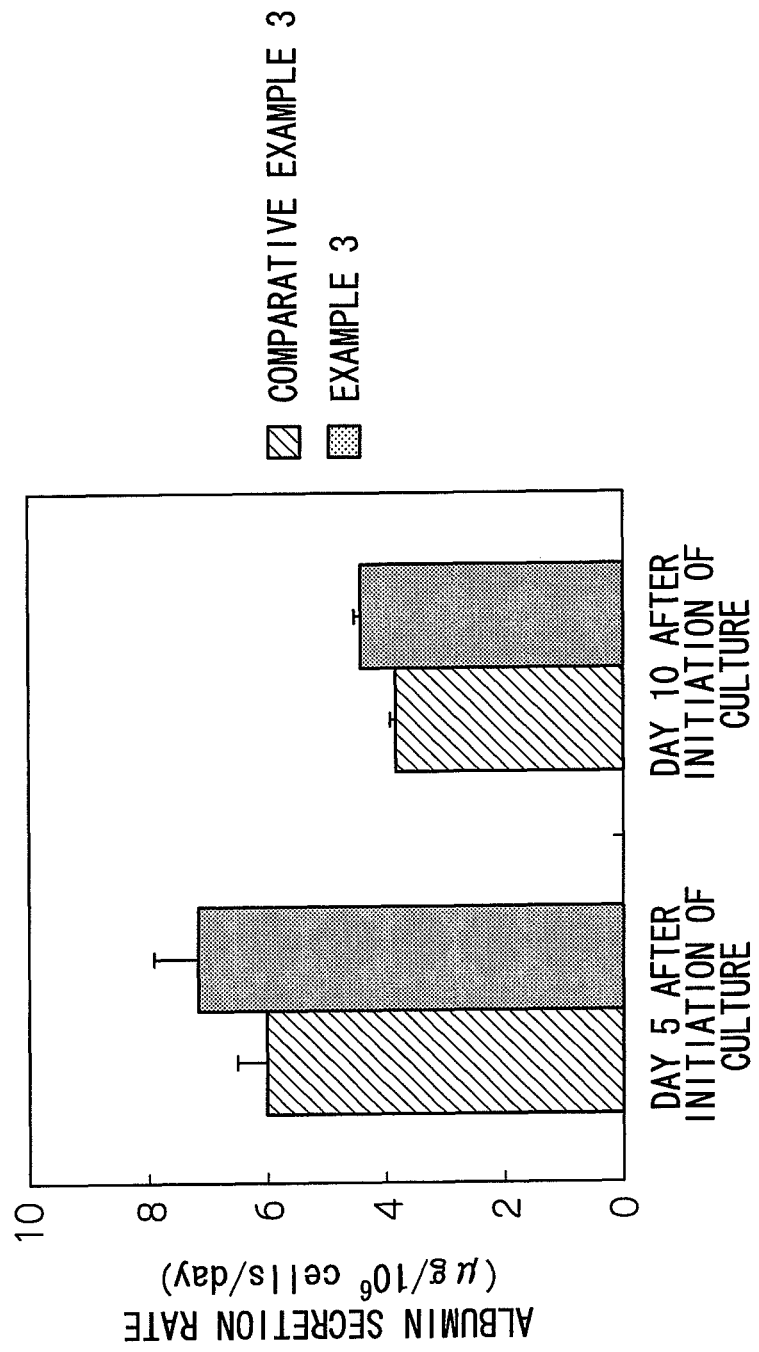
FIG. 12 is a graph showing the albumin secretion activity of constructs formed in Example 3 and Comparative example 3.

FIG. 8C shows the morphology of formed HuH7 cell spheroids, FIG. 9 shows the change in the spheroidal particle size and FIG. 12 shows the results of albumin secretion activity of HuH7 cells. The HuH7 cells formed regularly arranged spheroids on the tissue construct-forming kit A (see FIG. 8C). Further, while the spheroidal particle size increased as the cells proliferated at the initial stage of culture, on day 10 after initiation of culture and thereafter, the particle size was kept constant (FIG. 9). Further, from FIG. 12, it was found that the albumin secretion activity of HuH7 cells which were cultured to form a spheroid by the method for forming a tissue construct of the invention was higher compared with the case where a porous film was not used.

Example 4

As pancreatic proliferating cells, a RIN-5F cell line (Dainippon Sumitomo Pharma), which is a cell line derived from rat islets of Langerhans, was used. As the culture medium, a serum-containing culture medium obtained by adding 58.8 mg/L of penicillin (manufactured by Meiji Seika), 100 mg/L of streptomycin (manufactured by Meiji Seika), 2.2 g/L of sodium hydrogen carbonate (manufactured by Wako Pure Chemical Industries, Ltd.) and 10% of fetal bovine serum (FBS, manufactured by Invitrogen) to 8.4 g/L of RPMI-1640 medium (manufactured by SIGMA) was prepared and used. The cell morphology and change in the spheroidal particle size were evaluated in the same manner as in Example 1.

Figure 8D:
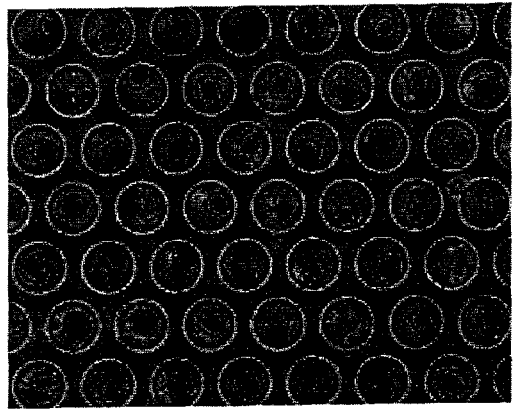

FIG. 8D shows the morphology of formed RIN-5F cell spheroids, and FIG. 9 shows the change in the spheroidal particle size. The RIN-5F cells formed regularly arranged spheroids on the tissue construct-forming kit A (see FIG. 8D). Further, it was shown that the spheroidal particle size increased as the cells proliferated at the initial stage of culture, however, on day 10 after initiation of culture and thereafter, the particle size was kept constant (FIG. 9).

Example 5

As undifferentiated cells, a 129SV cell line (Dainippon Sumitomo Pharma), which is a mouse ES cell line, was used. As the culture medium, a medium for ES cells (Dainippon Sumitomo Pharma) was used. The cell morphology and change in the spheroidal particle size were evaluated in the same manner as in Example 1.

Figure 8E:
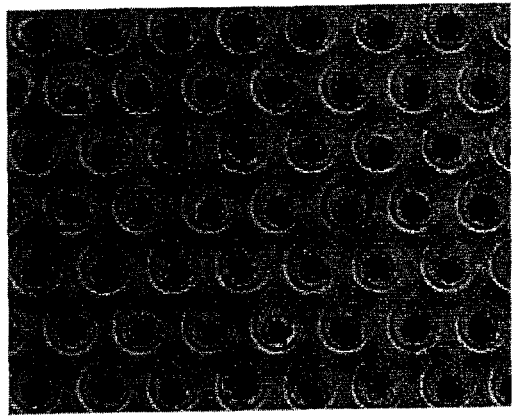

FIG. 8E shows the morphology of formed mouse ES cell spheroids, and FIG. 9 shows the change in the spheroidal particle size. The mouse ES cells formed regularly arranged spheroids on the tissue construct-forming kit A (see FIG. 8E). Further, while it was shown that the spheroidal particle size increased as the cells proliferated at the initial stage of culture, on day 5 after initiation of culture and thereafter, the particle size was kept constant (FIG. 9).

Example 6

A flat plate (24 mm×24 mm, thickness: 400 µm) made of polymethyl methacrylate (PMMA) was used as a supporting member 5a, and a pre-kit C as shown in FIG. 1 was produced. That is, a porous film, which was stamped in a grid pattern with a size of 5 mm×5 mm and produced in the same manner as in Example 1, was thermally compressed, whereby a pre-kit C having a plurality of hexagon sets, which can form cell adhesive regions 3a on the porous film surface as follows, formed thereon was produced.

In this pre-kit C, the porous film 1 is supported such that a space is formed on the back surface of the porous film 1 by fixing it at the vicinity of the center in the height direction of the supporting member 5a.

First, a platinum thin film was disposed on the surface of the pre-kit C in the same manner as in Example 1. Further, by using a stamp produced in the same manner as in Example 1, cell adhesive regions 3a were formed by applying collagen such that the diameter thereof was 100 µm and the position of the center point coincided with the position of the centroid point of a regular hexagon formed by connecting the center points of six adjacent regions, whereby a tissue construct-forming kit C was produced.

Figure 13A:
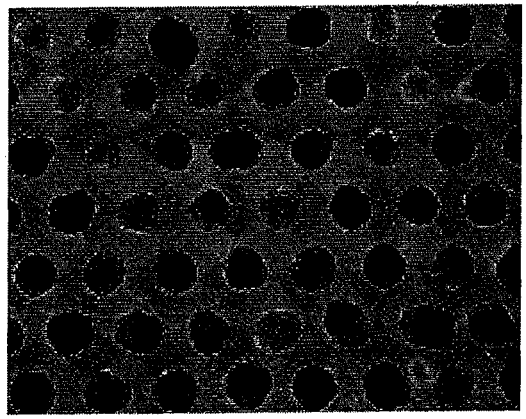
FIGS. 13A and 13B are light micrographs of constructs formed in Example 6.
Figure 13B:
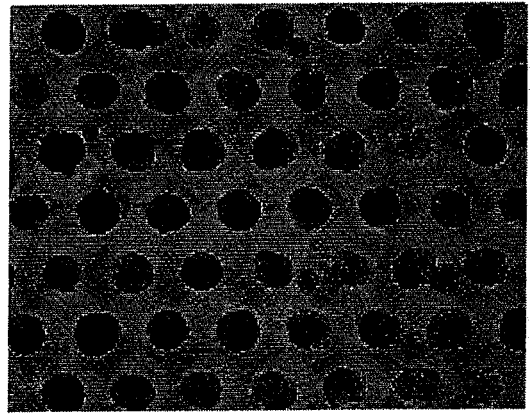

An experiment of culture of HepG2 cells was carried out in the same manner as in Example 2 except that the tissue construct-forming kit C was used in place of the tissue construct-forming kit A, and a state of forming a spheroid was observed using a phase contrast microscope. The microphotographs are shown in FIGS. 13A and 13B.

Further, a state of forming a spheroid 50 at this time is shown in schematic views of FIG. 14. The cell size of HepG2 cells is about 10 µm, however, as shown in FIG. 14A, in the case where a porous film with a pore size smaller than the cell size was used as the porous film 1, spheroids 50 were formed on both surfaces, i.e., on the surface 2 of the porous film 1 which is the surface inoculated with cells and the porous film surface (back surface) which is opposite to the surface inoculated with cells. A state of forming spheroids on the front surface (surface inoculated with cells) at this time is shown in FIG. 13A.

The case where culture was carried out in the same manner as above using a porous film with a pore size larger than the cell size as the porous film 1 is shown in FIG. 14B. A state for forming spheroids on the front surface (surface inoculated with cells) at this time is shown in FIG. 13B. In this case, spheroids 50 were formed not on the surface 2 of the porous film 1 on the side inoculated with cells, but on the porous film surface (back surface) opposite to the surface 2. These results show that the direction of formation of spheroids 50 can be controlled by the pore size of the porous film, which can be applied to studies related to anisotropy of culture environments and coculture systems.

The method for forming a tissue construct of the invention can provide an efficient method for forming a three-dimensional tissue construct which is capable of forming a three-dimensional tissue construct in which an increase in the size of the tissue construct is prevented even in the case where proliferating cells are cultured, and also maintaining the function of proliferating cells with a high metabolic activity over a long period of time. Accordingly, it is possible to provide a kit for studying three-dimensional culture of proliferating cells efficiently with high accuracy, and also to apply it to a simulator for reproducing biological behavior, an alternative technique for animal experiments in drug development, a regenerative medicine technique by cell transplantation and the like.

All publications, patent applications, and technical standards mentioned in this specification are herein incorporated by reference to the same extent as if such individual publication, patent application, or technical standard was specifically and individually indicated to be incorporated by reference. It will be obvious to those having skill in the art that many changes may be made in the above-described details of the preferred embodiments of the present invention. The scope of the invention, therefore, should be determined by the following claims.

What is claimed is:

1. A tissue construct-forming substrate, the substrate comprising a porous film having through-holes, and the porous film having, on each of a front surface and a back surface of the film, a plurality of cell adhesive regions capable of retaining cells and a cell non-adhesive region located at a peripheral region of each of the cell adhesive regions;
wherein the cell non-adhesive regions respectively form a continuous region, the porous film comprises the plural cell adhesive regions disposed such that adjacent cell adhesive regions are spaced a predetermined distance apart, and at least one of the through-holes is a transmission path that transfers a substance between the cell non-adhesive region on the front surface of the porous film and the cell non-adhesive region on the back surface of the porous film.

2. The tissue construct-forming substrate according to claim 1, wherein the shortest distance between one cell adhesive region and another cell adhesive region adjacent thereto is in the range of from 50 µm to 1000 µm.

3. The tissue construct-forming substrate according to claim 1, wherein the porous film comprises holes that communicate with one another and the size of the holes is from 0.01 µm to 100 µm.

4. The tissue construct-forming substrate according to claim 1, wherein the porous film having through-holes comprises a porous film having a three-dimensional reticulated structure.

5. The tissue construct-forming substrate according to claim 1, wherein the porous film comprises a porous film having voids formed therein obtained through film formation by casting a liquid containing an organic solvent and a polymeric compound onto a support.

6. The tissue construct-forming substrate according to claim 1, wherein the porous film comprises at least one selected from the group consisting of hydrophobic polymers and amphiphilic compounds.

7. The tissue construct-forming substrate according to claim 1, wherein the porous film comprises at least one amphiphilic compound selected from the group consisting of amphiphilic polymers and surfactants.

8. The tissue construct-forming substrate according to claim 1, further comprising a plurality of region sets, each of the region sets including one cell adhesive region and other cell adhesive regions adjacent thereto and separated by the cell non-adhesive region and the respective region sets having a different centroid distance.

9. The tissue construct-forming substrate according to claim 1, wherein the through-holes of the porous film are transmission paths that transfer a substance between the front and back surfaces of the porous film, between the cell adhesive regions on the front surface of the porous film and the cell non-adhesive region on the front surface of the porous film, and between the cell adhesive regions on the back surface of the porous film and the cell non-adhesive region on the back surface of the porous film.

10. A tissue construct-forming kit for forming a three-dimensional tissue construct containing proliferating cells, the kit comprising the tissue construct-forming substrate according to claim 1 and a frame which supports the tissue construct-forming substrate.

11. The tissue construct-forming kit according to claim 10, wherein the frame is a frame having a partition, vertically disposed on the surface of the tissue construct-forming substrate, for dividing the cell adhesive regions formed on the surface of the tissue construct-forming substrate.

12. The tissue construct-forming kit according to claim 10, wherein the porous film has a plurality of region sets including one region set which includes one cell adhesive region and other cell adhesive regions adjacent thereto and in which the centroid distance is a predetermined distance, and other region sets in which the centroid distance of the regions is different from that of the one region set.

13. A system including plural tissue construct-forming kits according to claim 12.

14. A tissue construct-forming substrate, the substrate comprising a porous film having through-holes, and the porous film having, on each of a front surface and a back surface of the film, a plurality of cell adhesive regions capable of retaining cells and a cell non-adhesive region located at a peripheral region of each of the cell adhesive regions, wherein the cell non-adhesive regions respectively form a continuous region, the porous film comprises the plural cell adhesive regions disposed such that adjacent cell adhesive regions are spaced a predetermined distance apart, and the through-holes of the porous film are transmission paths that transfer a substance between front and back surfaces of the porous film, between the cell adhesive regions on the front surface of the porous film and the cell non-adhesive region on the front surface of the porous film, and between the cell adhesive regions on the back surface of the porous film and the cell non-adhesive region on the back surface of the porous film.

* * * * *